(12) United States Patent
Düring et al.

(10) Patent No.: US 11,752,240 B2
(45) Date of Patent: *Sep. 12, 2023

(54) ROD SHAPED BODY AND MEDICAL DEVICE

(71) Applicant: MARVIS INTERVENTIONAL GMBH, Frechen (DE)

(72) Inventors: Klaus Düring, Frechen (DE); Joachim Georg Pfeffer, Aachen (DE)

(73) Assignee: MARVIS INTERVENTIONAL GMBH, Frechen (DE)

( * ) Notice: Subject to any disclaimer, the term of this patent is extended or adjusted under 35 U.S.C. 154(b) by 876 days.

This patent is subject to a terminal disclaimer.

(21) Appl. No.: 15/586,155

(22) Filed: May 3, 2017

(65) Prior Publication Data

US 2017/0232158 A1 Aug. 17, 2017

Related U.S. Application Data

(63) Continuation of application No. 13/880,032, filed as application No. PCT/EP2011/005230 on Oct. 18, 2011, now Pat. No. 9,656,004.

(30) Foreign Application Priority Data

Oct. 18, 2010 (EP) ..................... 10187863

(51) Int. Cl.
*A61L 31/12* (2006.01)
*A61M 25/09* (2006.01)
(Continued)

(52) U.S. Cl.
CPC ........ *A61L 31/128* (2013.01); *A61B 10/0233* (2013.01); *A61L 29/02* (2013.01);
(Continued)

(58) Field of Classification Search
CPC .............. A61B 10/0233; A61M 25/09; A61M 2025/09166; A61M 2025/09191;
(Continued)

(56) References Cited

U.S. PATENT DOCUMENTS 4,756,303 A 6/1988 Kawashima et al.
4,800,890 A * 1/1989 Cramer ................. A61M 5/007
600/434

(Continued)

FOREIGN PATENT DOCUMENTS

CA 2418790 A1 2/2003
DE 10040381 C1 6/2002
(Continued)

OTHER PUBLICATIONS

Chen, S., et al., "Engineered Biocompatible Nanoparticles for in Vivo Imaging Applications", "J. Am. Chem. Soc.", Oct. 4, 2010, pp. 15022-15029, vol. 132.

(Continued)

*Primary Examiner* — Rene T Towa
(74) *Attorney, Agent, or Firm* — HULTQUIST, PLLC; Steven J. Hultquist

(57) ABSTRACT

The present invention relates to a medical device. In particular, the present invention concerns a medical device which can be detected by means of magnetic resonance imaging (MRI).

14 Claims, 15 Drawing Sheets

Figure 1A:
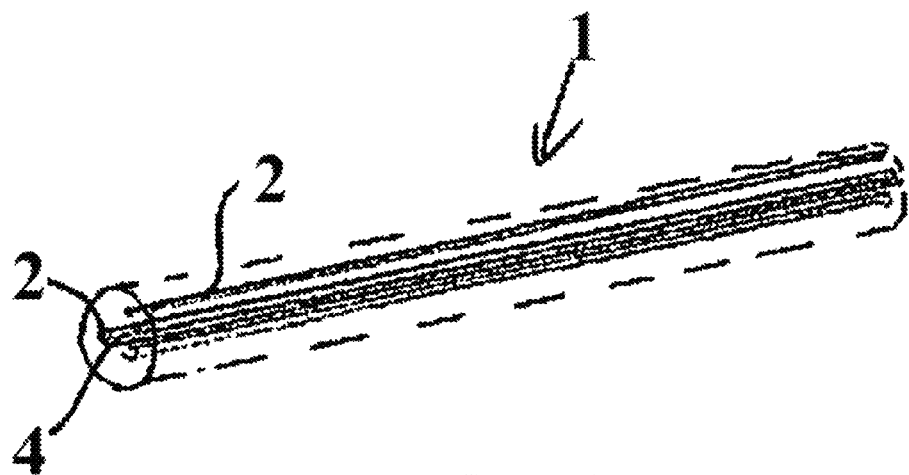

(51) Int. Cl.

| | |
|---|---|
| *A61L 29/12* | (2006.01) |
| *A61L 29/18* | (2006.01) |
| *A61L 31/18* | (2006.01) |
| *A61B 10/02* | (2006.01) |
| *A61L 29/02* | (2006.01) |
| *A61L 29/04* | (2006.01) |
| *A61L 29/14* | (2006.01) |
| *A61L 31/02* | (2006.01) |
| *A61L 31/04* | (2006.01) |
| *A61L 31/14* | (2006.01) |
| *A61M 5/32* | (2006.01) |

(52) U.S. Cl.
CPC ........... *A61L 29/049* (2013.01); *A61L 29/126* (2013.01); *A61L 29/14* (2013.01); *A61L 29/18* (2013.01); *A61L 31/022* (2013.01); *A61L 31/041* (2013.01); *A61L 31/125* (2013.01); *A61L 31/14* (2013.01); *A61L 31/18* (2013.01); *A61M 5/32* (2013.01); *A61M 25/09* (2013.01); *A61M 2025/09166* (2013.01); *A61M 2025/09191* (2013.01); *Y10T 428/2933* (2015.01); *Y10T 428/2964* (2015.01); *Y10T 428/2969* (2015.01)

(58) Field of Classification Search
CPC ................ A61M 5/32; A61M 25/0045; A61M 2025/09133; Y10T 428/2969; Y10T 428/2964; Y10T 428/2933; A61L 31/18; A61L 31/14; A61L 31/125; A61L 31/041; A61L 31/022; A61L 31/128; A61L 29/18; A61L 29/14; A61L 29/126; A61L 29/049; A61L 29/02
See application file for complete search history.

(56) References Cited

U.S. PATENT DOCUMENTS

| | | | |
|---|---|---|---|
| 5,154,179 A | 10/1992 | Ratner | |
| 6,099,485 A | 8/2000 | Patterson | |
| 6,451,026 B1* | 9/2002 | Biagtan ................. | A61M 25/09 600/585 |
| 6,458,088 B1 | 10/2002 | Hurtak et al. | |
| 7,531,122 B2* | 5/2009 | Weber ..................... | B29C 65/32 264/491 |
| 9,656,004 B2 | 5/2017 | Duering et al. | |
| 2003/0004563 A1 | 1/2003 | Jackson et al. | |
| 2003/0055449 A1 | 3/2003 | Lee et al. | |
| 2003/0099764 A1 | 5/2003 | Li et al. | |
| 2005/0234336 A1* | 10/2005 | Beckman ............... | A61B 90/39 600/431 |
| 2006/0118319 A1* | 6/2006 | Wang ..................... | B82Y 25/00 174/36 |
| 2007/0050032 A1* | 3/2007 | Gittings ................ | A61F 2/4425 623/17.12 |
| 2008/0015558 A1* | 1/2008 | Harlan .................. | A61M 25/09 606/15 |
| 2008/0125674 A1 | 5/2008 | Bilecen et al. | |
| 2009/0299332 A1* | 12/2009 | Shireman .............. | A61M 25/09 604/526 |
| 2010/0063379 A1 | 3/2010 | Pfeffer et al. | |
| 2011/0166349 A1 | 7/2011 | Bertrand et al. | |
| 2011/0166439 A1 | 7/2011 | Pfeffer et al. | |

FOREIGN PATENT DOCUMENTS

| | | | | |
|---|---|---|---|---|
| DE | 10107750 | A1 | 11/2003 | |
| EP | 0659056 | B1 | 6/1995 | |
| EP | 1206945 | A1 | 5/2002 | |
| EP | 1388346 | B1 | 4/2006 | |
| EP | 1818054 | A1 | 8/2007 | |
| WO | 8702893 | A1 | 5/1987 | |
| WO | 9423782 | A1 | 10/1994 | |
| WO | 9717622 | A1 | 5/1997 | |
| WO | 9960920 | A2 | 12/1999 | |
| WO | 0195794 | A1 | 12/2001 | |
| WO | 0222186 | A1 | 3/2002 | |
| WO | 03000307 | A1 | 1/2003 | |
| WO | 2005120598 | A1 | 12/2005 | |
| WO | 2007000148 | A2 | 1/2007 | |
| WO | 2007000148 | A3 | 1/2007 | |
| WO | 2009141165 | A2 | 11/2009 | |
| WO | 2009141165 | A3 | 11/2009 | |
| WO | WO-2009141165 | A2 * | 11/2009 | ............ A61L 31/18 |

OTHER PUBLICATIONS

"NOTE: For the non-patent literature citations that no month of publication is indicated, the year of publication is more than 1 year prior to the effective filing date of the present application."

Ratnayaka, K., et al., "Interventional cardiovascular magnetic resonance: still tantalizing", "Journal of Cardiovascular Magnetic Resonance", Dec. 29, 2008, pp. (Full Copy Not Provided; Abstract Within Specification p. 25).

Storch, D., "Neue, radioaktiv markierte Magnet-Resonanz-aktive Somatostatinanaloga zur besseren Diagnose und zielgerichteten Radionuklidtherapie von neuroendokrinen Tumoren", "Chapter 1.6.1 of Dissertation", 2005, pp. (Full Copy Not Provided; Abstract Within Specification p. 2), Published in: Basel, Switzerland.

Umathum, R., et al., "Rubber Materials for Active Device Tracking", "Abstract 16th ISMRM Congress", 2008, Page(s) (Full Copy Not Provided; Abstract Within Specification p. 33), Published in: Toronto, Canada.

* cited by examiner

A1  A2 
B1  B2 
FIG. 4C

A1   A2 
B1 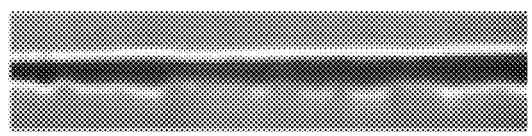  B2 
FIG. 4D

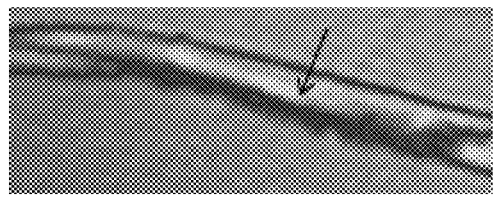
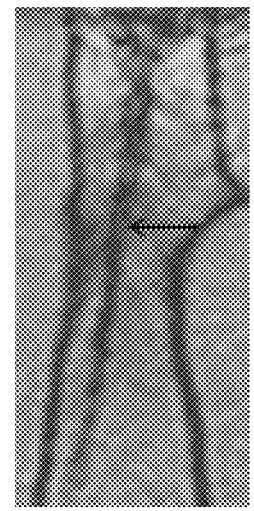
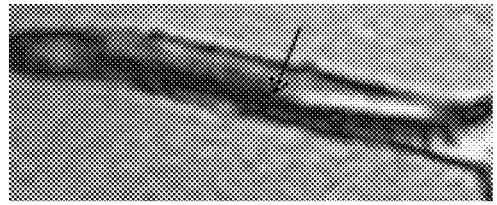
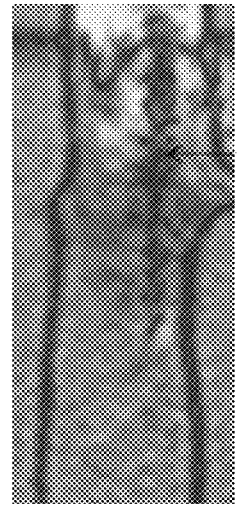
FIG. 4E

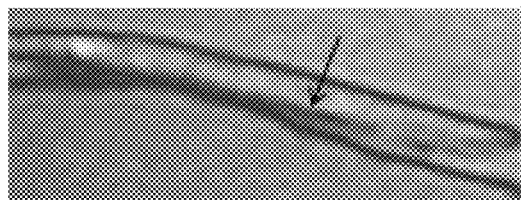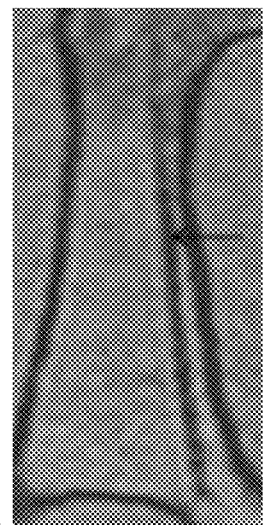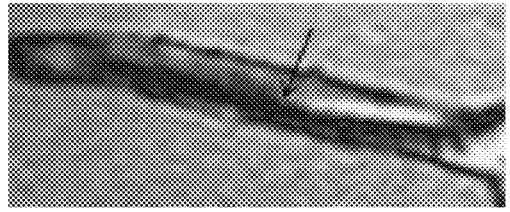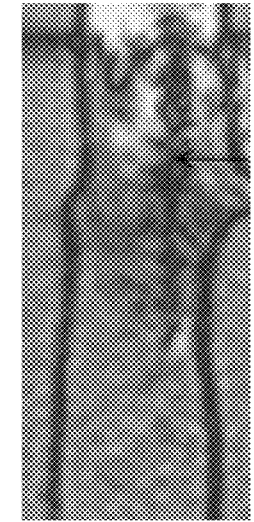
FIG. 4F

| Name of medical instrument | Design of instrument | Design of rods | Interventional applications |
|---|---|---|---|
| Guidewire (A) | 1 central rod (1/1), 6 peripheral rods (1/2), outer diameter: 0.97 mm; envelope polymer: Tecoflex EG-72D or similar, alternatively Mediprene with similar shore hardness | rod (1/1): 66Tex glass fiber, epoxy resin, diameter: 0.24 mm; rod (1/2): 33Tex glass fiber, epoxy resin, diameter: 0.17 mm | stiff guidewire for: aortic stenting liver puncture renal puncture |
| Guidewire (B) | 1 central rod (1/1), 6 peripheral rods (1/2), outer diameter: 0.81 – 0.89 mm; envelope polymer: Tecoflex EG-60D or similar, alternatively Mediprene with similar shore hardness | rod (1/1): 66Tex glass fiber, epoxy resin, diameter: 0.24 mm; rod (1/2): 33Tex glass fiber, epoxy resin, diameter: 0.17 mm | medium to stiff guidewire for: angiography in larger vessels |
| Guidewire (C) | 1 central rod (1/1), 3 peripheral rods (1/2), outer diameter: 0.81 – 0.89 mm; envelope polymer: Tecoflex EG-60D or similar, alternatively Mediprene with similar shore hardness | rod (1/1): 33Tex glass fiber, epoxy resin, diameter: 0.20 mm; rod (1/2): 33Tex glass fiber, epoxy resin, diameter: 0.17 mm | medium guidewire for: angiography in peripheral and visceral vessels |
| Guidewire (D) | 1 central rod (1/1), 3 peripheral rods (1/2), outer diameter: 0.30 – 0.40 mm; envelope polymer: Tecoflex EG-60D or similar, alternatively Mediprene with similar shore hardness | rod (1/1): 33Tex glass fiber, epoxy resin, diameter: 0.17 mm; rod (1/2): 16Tex glass fiber, epoxy resin, diameter: 0.10 mm | flexible guidewire for: neuroradiology and cardiology |
| Guidewire (E) | 3 rods (1/1), outer diameter: 0.25 – 0.30 mm; envelope polymer: Tecoflex EG-60D similar, alternatively Mediprene with similar shore hardness | rod (1/1): 16Tex glass fiber, epoxy resin, diameter: 0.10 mm | super flexible guidewire for: neuroradiology and cardiology |
| Guidewire (F) | 3 rods (1/1), outer diameter: 0.25 – 0.30 mm; envelope polymer: Tecoflex EG-85A similar, alternatively Mediprene with similar shore hardness | rod (1/1): 16Tex glass fiber, epoxy resin, diameter: 0.10 mm | super flexible guidewire for: neuroradiology and cardiology |
| Catheter (A) | outer diameter: 5F (1.7 mm), inner diameter: 1.10 mm, wall thickness: 0.30 mm; 3 rods (1), polymer: Tecoflex EG-60D or similar, alternatively Mediprene with similar shore hardness | rod (1): 33Tex glass fiber, epoxy resin, diameter: 0.17 mm | standard diagnostic / angiography catheter |
| Catheter (B) | outer diameter: 5F (1.7 mm), inner diameter: 1.10 mm, wall thickness: 0.30 mm; 5 rods (1), polymer: Tecoflex EG-60D or similar, alternatively Mediprene | rod (1): 33Tex glass fiber, epoxy resin, diameter: 0.17 mm | standard diagnostic / angiography catheter |

FIG. 5A

| Name of medical instrument | Design of instrument | Design of rods | Interventional applications |
|---|---|---|---|
| | with similar shore hardness | | |
| Catheter (C) | outer diameter: 5F (1.7 mm), inner diameter: 1.10 mm, wall thickness: 0.30 mm; 3 rods (1), polymer: Tecoflex EG-85A or similar, alternatively Mediprene with similar shore hardness | rod (1): 33Tex glass fiber, epoxy resin, diameter: 0.17 mm | standard diagnostic / angiography catheter |
| Catheter (D) | outer diameter: 5F (1.7 mm), inner diameter: 1.10 mm, wall thickness: 0.30 mm; 5 rods (1), polymer: Tecoflex EG-85A or similar, alternatively Mediprene with similar shore hardness | rod (1): 33Tex glass fiber, epoxy resin, diameter: 0.17 mm | standard diagnostic / angiography catheter |
| Catheter (E) | outer diameter: 5F (1.7 mm), inner diameter: 1.30 mm, wall thickness: 0.20 mm; 3 rods (1), polymer: Tecoflex EG-60D or similar, alternatively Mediprene with similar shore hardness | rod (1): 33Tex glass fiber, epoxy resin, diameter: 0.17 mm | standard diagnostic / angiography catheter |
| Catheter (F) | outer diameter: 5F (1.7 mm), inner diameter: 1.10 mm, wall thickness: 0.30 mm; 5 rods (1), polymer: Tecoflex EG-60D or similar, alternatively Mediprene with similar shore hardness | rod (1): 33Tex glass fiber, epoxy resin, diameter: 0.17 mm | standard diagnostic / angiography catheter |
| Catheter (G) | outer diameter: 5F (1.7 mm), inner diameter: 1.30 mm, wall thickness: 0.20 mm; 3 rods (1), polymer: Tecoflex EG-85A or similar, alternatively Mediprene with similar shore hardness | rod (1): 33Tex glass fiber, epoxy resin, diameter: 0.17 mm | standard diagnostic / angiography catheter |
| Catheter (H) | outer diameter: 5F (1.7 mm), inner diameter: 1.10 mm, wall thickness: 0.30 mm; 5 rods (1), polymer: Tecoflex EG-85A or similar, alternatively Mediprene with similar shore hardness | rod (1): 33Tex glass fiber, epoxy resin, diameter: 0.17 mm | standard diagnostic / angiography catheter |
| Catheter (I) | outer diameter: 4F (1.32 mm), inner diameter: 1.10 mm, wall thickness: 0.22 mm; 3 rods (1), polymer: Tecoflex EG-60D or similar, alternatively Mediprene with similar shore hardness | rod (1): 16Tex glass fiber, epoxy resin, diameter: 0.10 mm | small diameter diagnostic / angiography catheter |
| Catheter (K) | outer diameter: 4F (1.32 mm), inner diameter: 1.10 mm, wall thickness: 0.22 mm; 5 rods (1), polymer: Tecoflex EG-60D or similar, alternatively Mediprene with similar shore hardness | rod (1): 16Tex glass fiber, epoxy resin, diameter: 0.10 mm | small diameter diagnostic / angiography catheter |
| Catheter (L) | outer diameter: 4F (1.32 mm), inner diameter: 1.10 mm, wall | rod (1): 16Tex glass fiber, epoxy resin, diameter: | small diameter diagnostic / |

FIG. 5B

| Name of medical instrument | Design of instrument | Design of rods | Interventional applications |
|---|---|---|---|
|  | thickness: 0.22 mm; 3 rods (1), polymer: Tecoflex EG-85A or similar, alternatively Mediprene with similar shore hardness | 0.10 mm | angiography catheter |
| Catheter (M) | outer diameter: 4F (1.32 mm), inner diameter: 1.10 mm, wall thickness: 0.22 mm; 5 rods (1), polymer: Tecoflex EG-85A or similar, alternatively Mediprene with similar shore hardness | rod (1): 16Tex glass fiber, epoxy resin, diameter: 0.10 mm | small diameter diagnostic / angiography catheter |
| Catheter (N) | outer diameter: 2.5F (0.83 mm), inner diameter: 0.53 mm, wall thickness: 0.15 mm; 3 rods (1), polymer: Tecoflex EG-60D or similar, alternatively Mediprene with similar shore hardness | rod (1): 12Tex glass fiber, epoxy resin, diameter: 0.08 mm | microcatheter, e.g. for tumor therapy, neuroradioloy |
| Catheter (O) | outer diameter: 2.5F (0.83 mm), inner diameter: 0.53 mm, wall thickness: 0.15 mm; 5 rods (1), polymer: Tecoflex EG-60D or similar, alternatively Mediprene with similar shore hardness | rod (1): 12Tex glass fiber, epoxy resin, diameter: 0.08 mm | microcatheter, e.g. for tumor therapy, neuroradioloy |
| Catheter (P) | outer diameter: 2.5F (0.83 mm), inner diameter: 0.53 mm, wall thickness: 0.15 mm; 3 rods (1), polymer: Tecoflex EG-85A or similar, alternatively Mediprene with similar shore hardness | rod (1): 12Tex glass fiber, epoxy resin, diameter: 0.08 mm | microcatheter, e.g. for tumor therapy, neuroradioloy |
| Catheter (Q) | outer diameter: 2.5F (0.83 mm), inner diameter: 0.53 mm, wall thickness: 0.15 mm; 5 rods (1), polymer: Tecoflex EG-85A or similar, alternatively Mediprene with similar shore hardness | rod (1): 12Tex glass fiber, epoxy resin, diameter: 0.08 mm | microcatheter, e.g. for tumor therapy, neuroradioloy |
| Puncture needle (A) | outer diameter: 2.1 mm, inner diameter: 1.5 mm, wall thickness: 0.3 mm; 6 rods (1), polymer: epoxy resin | rod (1): 33Tex glass fiber, epoxy resin, diameter: 0.17 mm | standard puncture needle, e.g. for tumor therapy |
| Puncture needle (B) | outer diameter: 1.2 mm, inner diameter: 0.9 mm, wall thickness: 0.15 mm; glass fibers directly embedded in epoxy resin | -- | micro puncture needle, e.g. for tumor therapy |

FIG. 5C

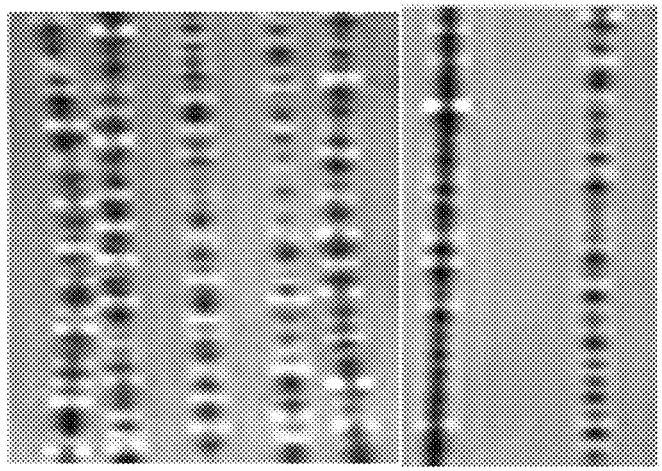
1 2 3 4 5 6 7
A
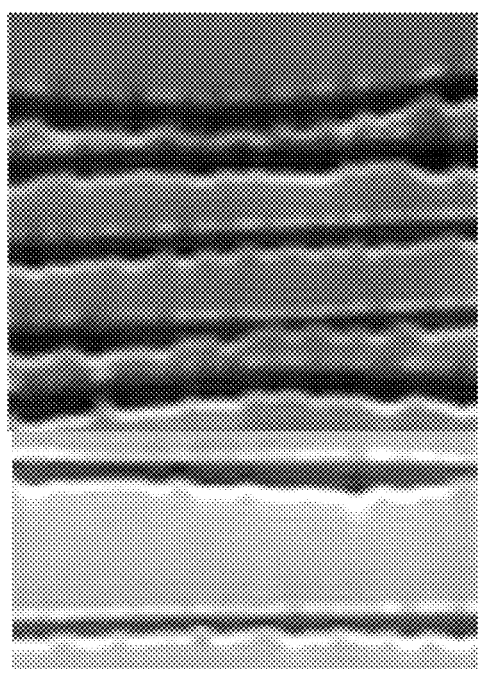
1
2
3
4
5
6
7
B
FIG. 6

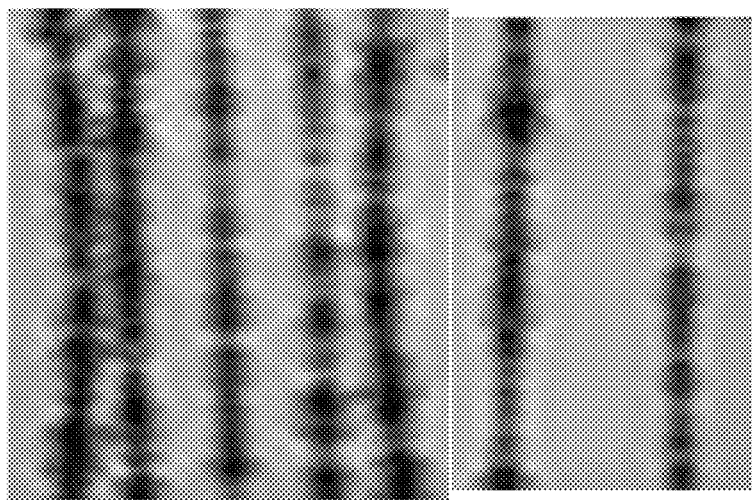
1 2 3 4 5 6 7
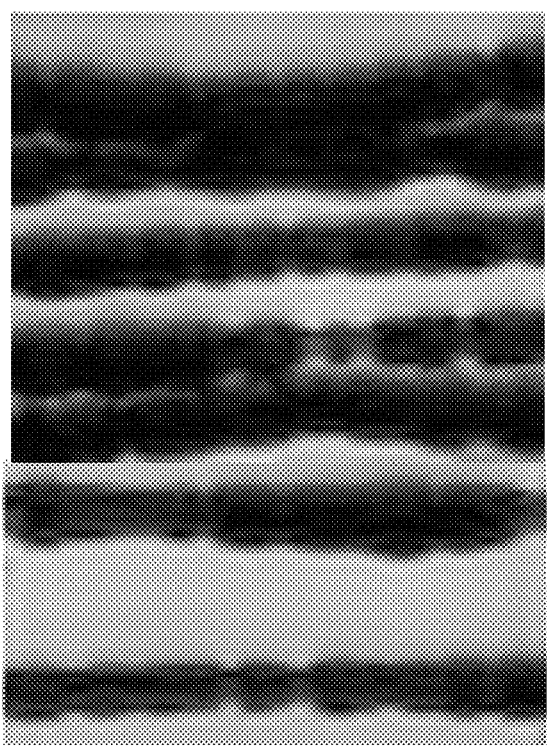
1
2
3
4
5
6
7
FIG. 7

ROD SHAPED BODY AND MEDICAL DEVICE

CROSS-REFERENCE TO RELATED APPLICATIONS

This is a continuation of U.S. patent application Ser. No. 13/880,032 filed on Apr. 17, 2013, which is a U.S. national phase under the provisions of 35 U.S.C. § 371 of International Patent Application No. PCT/EP11/05230 filed Oct. 18, 2011, which in turn claims priority of European Patent Application No. 10187863.5 filed Oct. 18, 2010. The disclosures of all such applications are hereby incorporated herein by reference in their respective entireties, for all purposes.

The present invention relates to a rod shaped body and a medical device. In particular, the present invention concerns a medical device which can be detected by means of magnetic resonance imaging (MRI).

WO 2007/000148 A2 discloses a rod shaped body serving for the design of medical devices such as catheters or guidewires. This rod shaped body consists of one or more filaments and a non-ferromagnetic matrix material enclosing the filaments. A doping agent made of particles which create MRI artifacts is embedded in the matrix material.

A detailed explanation of MRI can be found in the Internet at http://en.wikipedia.org/wiki/Magnetic_Resonance_Imaging.

DE 101 07 750 A1 describes a guidewire which is supposed to be suitable for MRI. This guidewire comprises a core made of a metallic distal part. Cords made from an electrically non-conductive polymer material are arranged between an outer jacket and the core. This polymer material is supposed to be reinforced with glass fibers or carbon fibers. Carbon fibers, however, are electrical conductors so that they cannot be used in MRI.

Further medical devices are known from EP 1 206 945A1. These are equipped with paramagnetic metallic compounds and/or a paramagnetic metal so that they are visible in MRI.

EP 0 659 056 B1 discloses a contrast agent adapted for MRI of a sample. This contrast agent comprises a suspension of particles possessing positive magnetic susceptibility characteristics and particles possessing negative magnetic susceptibility characteristics. The relative amounts of these two kinds of particles are adjusted such that the positive magnetic susceptibility offsets the negative magnetic susceptibility to such an extent that the resulting suspension has substantially zero magnetic susceptibility. This eliminates substantially all imaging artifacts and delimitates the signal or artifact, respectively, almost sharply to the object itself.

WO 87/02893 discloses poly-chelating substances for imaging enhancement and spectral enhancement for MRI. These substances comprise different complexes in which metal ions, in particular gadolinium ions, are immobilized.

The relaxivity of gadolinium(III) complexes is explained in chapter 1.6.1 of the Ph.D thesis (Inaugural Dissertation) by Daniel Storch, entitled "Neue, radioaktiv markierte Magnet-Resonanz-aktive Somatostatinanaloga zur besseren Diagnose and zielgerichteten Radionuklidtherapie von neuroendokrinen Tumoren", Basel, 2005. The paramagnetic relaxation of the water molecules located in the vicinity of the gadolinium(III) ion is the result of the dipole-dipole-interaction between the nuclear spin and the fluctuating local magnetic field of the MRI scanner, caused by the unpaired electrons of the gadolinium(III) ion. The magnetic field around the paramagnetic center, i.e. the gadolinium(III) ion, decreases with increasing distance. Therefore, it is essential to locate the protons in close proximity to the metal ion. For gadolinium(III) complexes this means that the water molecules are to be transported into the first coordination sphere of the metal ion. These "inner-sphere" $H_2O$ molecules are exchanged with the surrounding water molecules and in this way transmit the paramagnetic effect.

DE 100 40 381 C1 discloses fluoroalkyl-containing complexes with residual sugars. These complexes can be provided with paramagnetic metal ions so that they can serve as contrast agents in magnetic resonance imaging. These metal ions are in particular the bivalent and trivalent ions of the elements of the atomic numbers 21 to 29, 42, 44 and 58 to 70. Suitable ions are, for instance, the chromium(III), iron (II), cobalt(II), nickel(II), copper(II), praseodymium(III), neodymium(III), samarium(III) and ytterbium(III) ions. Gadolinium(III), erbium(III), dysprosium(III), holmium (III), erbium(III), iron(III) and manganese(II) ions are particularly preferred because of their strong magnetic moment.

EP 1 818 054 A1 discloses the use of gadolinium chelates for the purpose of marking cells.

U.S. Pat. No. 6,458,088 B1 describes a guidewire provided for MRI, this guidewire comprising a glass body. The glass body is provided with a protective layer which is made of polymeric material and additionally can be reinforced with fibers. The distal end of the guidewire can be made from a metal section such as nitinol. This metal section should have a length which is clearly shorter than the wavelength of the magnetic resonance field.

WO 2005/120598A1 discloses a catheter guidewire comprising a PEEK core. This core is covered by a coating. The coating contains a contrast agent. The contrast agent is iron powder having a grain size of less than 10 µm.

WO 97/17622 discloses a medical device comprising an electrically non-conductive body which is covered by an ultra-thin coating made of an electrically conductive material so that the medical device is visible in MRI without unduly affecting the image.

WO 99/060920A2 and WO 2002/022186A1 each describe a coating for a medical device comprising a paramagnetic ion which is complexed in the coating. The paramagnetic ion in particular is gadolinium. This coating is visible in MRI.

WO 2009/141165 A2 discloses a medical device which can be inserted into a human or animal body. The medical device has a body which comprises at least one rod shaped body having poor electrical conductivity and being formed from a matrix material and non-metallic filaments. These rod shaped bodies correspond insofar to the one described in WO 2007/000148 A2.

The rod shaped body is doped with X-ray marker particles and the medical device further comprises an MR marker. The MR marker can be provided by means of a further rod shaped body or by means of an immobilized active MR marker on the surface area of the medical device.

Such rod shaped bodies are very advantageous for use in medical devices which can be readily produced by embedding one or more such rod shaped bodies in an envelope polymer wherein the rod shaped bodies may contain different doping materials. By using different types of rod shaped bodies medical devices having different doping materials (=markers) can be designed and produced. Hence, these have different properties with respect to their visibility in X-ray or MRI examinations. These different medical devices can be produced by the very same production method and consecutively in the same production run by simply exchanging one or several of the rods. Therefore, even if these medical devices are produced in small quantities it is possible to economically manufacture different types of medical devices.

In Shu Chen et al.; "Engineered Biocompatible Nanoparticles for in Vivo Imaging Applications"; American Chemical Society 2010, 132, 15022-15029, the use of FePt nanoparticles as contrast agent for MRI is described.

One object of the present invention is to further improve such rod shaped bodies for being embedded in a matrix material of a medical device.

A further object of the present invention is to provide such rod shaped body or a medical device comprising at least one such rod shaped body which can be employed safer than the known medical devices.

A further object of the present invention is to provide such rod shaped body or a medical device having optimized markers.

A further object of the present invention is to provide a medical device which can be inserted into a human or animal body and is very versatile in its use in MRI examinations.

A further object of the present invention is a medical device having a coating stably attached to the outer surface.

The subject matter of the independent claims solve one or more of these objects.

Advantageous embodiments are indicated in the subclaims.

Throughout the specification the term "medical device" is used in a broad sense to refer to any medicinal device, tool, instrument or other object. The medical devices of the present invention are particularly useful as any type of guidewires, catheters (including vascular and non-vascular, esophageal, peritoneal, peridural, nephrostomy catheters), tubes, mandrins, stylets, stents, implants, grafts, biopsy needles, puncture needles, cannulae, intralumenal medical devices, endotracheal tubes, and ablation devices. They can be introduced or implanted in a "target" or "target object". The target or target object is all or a part of the human or animal body. The medical device of the present invention particularly may be brought into cavities of the target (object). These cavities are particularly blood vessels, neuronal ways, any organs (whole or part) or tissues (whole or part). The medical device of the present invention may also be used as an accessory part providing MRI functionality and/or applicability to other medical devices.

According to a first aspect a rod shaped body comprises
one or more non-metallic filaments and
a non-ferromagnetic matrix material,
wherein the matrix material encloses and/or agglutinates the filaments,
and marker particles for generating a signal in an X-ray or magnetic resonance imaging process,
wherein at least one of said non-metallic filaments is a ht-fiber.

A ht-fiber is a high tenacity fiber. Typical examples of ht-fibers are aramide fibers and UHMWPE fibers (ultra high molecular weight polyethylene fibers). Ht-fibers have a tensile strength of at least 20 cN/tex. Optionally the ht-fibers have a tensile strength (tenacity) of at least 23 cN/tex and in particular of at least 30 cN/tex.

A ht-fiber is highly flexible and provides a high tensile strength. Thereby, it is ensured that even if the rod breaks in the human or animal body during the medical intervention the broken parts are still connected by the ht-fiber and can be safely pulled out.

Furthermore, the ht-fiber provides a certain rigidity to the rod. However, glass fibers are stiffer than ht-fibers so that a rod having both ht-fibers and glass fibers is preferred. Such a rod can be optimally adjusted with respect to rigidity versus flexibility and with respect to torsional stiffness.

According to a second aspect of the present invention, a rod shaped body comprises
one or more non-metallic filaments and
a non-ferromagnetic matrix material,
wherein the matrix material encloses and/or agglutinates the filaments, and marker particles for generating a signal in an X-ray or MRI process. This rod shaped body is characterized in that the one or more non-metallic filaments extend along the major part of the rod shaped body.

Such long filaments provide a high strength in longitudinal direction to the rod shaped bodies.

The non-metallic filaments are electrically non-conductive filaments so that they can be used during MRI measurements. Concluding, the term "non-metallic filaments" as used in the present text excludes any electrically conductive filaments such as a thin metal wire or a carbon filament.

Advantageously the filaments form a roving which comprises several filaments being arranged in parallel to each other.

However, it is also possible that the filaments of a rod shaped body form a yarn which means that the filaments are drilled and/or braided.

According to a further aspect of the present invention a medical device comprises one or more rod shaped bodies, each comprising
one or more non-metallic filaments and
a non-ferromagnetic matrix material,
wherein the matrix material encloses and/or agglutinates the filaments and marker particles for generating a signal in an X-ray or magnetic resonance imaging process,
and an envelope polymer in which the one or more rod shaped bodies are embedded,
wherein a cord is embedded either in the matrix material or in the envelope polymer, wherein the cord is more flexible than the non-metallic filaments.

The stiffness of the medical devices and hence of the rod shaped bodies in lateral direction has to be in a certain range which allows to easily guide the medical device through a given cavity of the human or animal body, e.g. a blood vessel. Therefore, the lateral stiffness is limited and it can occur under extreme conditions that the non-metallic filament(s) in the rod(s) may break. In such a case the broken parts of the rod(s) are still connected by the cord whereby additionally the envelope polymer remains intact. The medical device still can be safely removed as one part from the body cavity without the risk of lost parts in the blood stream or in body tissue. Thus the cord represents a means for increased safety of the medical devices.

The cord preferably is a thin cord having a high tensile strength. Suitable cords are e.g. polyamide filaments, ht-fibers, polyethylene terephthalate (PET) filaments, rayon filaments (e.g. HL fiber), cotton filaments, or hemp filaments having a diameter preferably of 0.05 mm to 0.2 mm. If the cord comprises one or more ht-fibers then these ht-fibers can simultaneously act as the non-metallic filaments of the rod shaped body. Of course it is possible to provide the cord in the medical device independent of the rod shaped bodies of said device.

According to another aspect of the present invention a medical device comprises several rod shaped bodies, each comprising
one or more non-metallic filaments and
a non-ferromagnetic matrix material, wherein the matrix material encloses and/or agglutinates the filaments and marker particles for generating a signal in an X-ray or magnetic resonance imaging process, and an envelope polymer in which the rod shaped bodies are embedded, wherein the rod shaped bodies are arranged in different positions with respect to the center of the medical device and the rod shaped bodies which are positioned closer to the center of the medical device comprise non-metallic filaments having a higher tensile modulus than the nonmetallic filaments of the rod shaped bodies which are positioned more distant to the center of the medical device.

Such a medical device having non-metallic filaments with a higher strength in the rods in its center section than the strength of the non-metallic filaments of the rods in the more peripheral section combines both a high flexibility as well as a high strength.

According to a further aspect the medical device comprises an elongated body, such as a guidewire, catheter or tube, made of a polymer material and the polymer material encloses a passive-negative MRI marker consisting of marker particles for generating an artifact in a magnetic resonance imaging process, wherein the passive-negative MRI marker is located only in a central section of the medical device.

As the marker is located in a central section it is covered by a circumferential section which does not contain any MRI marker. Therefore, there is a certain distance between the MRI marker and the outer surface of the medical device. In use the MRI marker is kept in this distance to water molecules surrounding the medical device. The larger this distance is the smaller are the artifacts in the MRI imaging process.

The distance of the passive-negative MRI marker to the outer surface of the medical device is preferably at least 0.1 mm, more preferably at least 0.2 mm, or at least 0.3 mm.

Such a medical device can comprise non-metallic filaments and said polymer material forms a non-ferromagnetic matrix material enclosing and/or agglutinating the filaments.

Such a medical device can also comprise the above described rod shaped bodies containing said MRI marker.

Such a medical device can be a guidewire having a rod shaped body comprising a passive-negative MRI marker and being positioned at the center of the guidewire.

Such a device can also be a catheter or a tube having either at least one rod shaped body comprising a passive-negative MRI marker and being positioned at the inner section of the catheter or the tube, or is embodied of at least two concentric layers, wherein only the innermost layer comprises a passive-negative MRI marker.

If the medical device is embodied as said catheter or tube having at least two concentric layers, one of said layers can be reinforced by non-metallic filaments being twisted, braided, or woven to a spatial structure. Such a spatial structure is particularly preferable in combination with ht-fibers. Ht-fibers are flexible and have a high tensile strength. As in such a spatial structure the filaments are running in different directions in the body of the medical device the high tensile strength causes also a high stiffness of the composite material consisting of the fibers and the matrix material.

According to a further aspect of the present invention a medical device comprises several rod shaped bodies for reinforcing the medical device, and an envelope polymer in which the rod shaped bodies are embedded, wherein the medical device comprises marker particles for generating an artifact in an MRI process, and the envelope polymer is a soft polymer or rubber material or PVC.

The rod shaped bodies according to this aspect of the invention can be embodied according to the other aspects of the present invention and/or the non-metallic reinforcing filaments may be glass fibers.

The markers can be incorporated into the rods and/or into the envelope polymer.

The specific envelope polymer according to this further aspect of the present invention has a relaxation time significantly shorter than that of water but distinctly longer than that of a hard polymer such as epoxy resin. Therefore, different from hard polymers, with appropriate parameter settings and a short echo time (preferably <100 ms, more preferably <50 ms, even more preferably <10 ms, and most preferably <1 ms) this envelope polymer can be visualized in an MRI process. Particularly, the protons of this envelope polymer can be detected with an MRI echo time that is different from the one used for detecting the protons of water. Therefore, by using two different echo times it is possible to record two different images of the same object with the same view wherein one image clearly visualizes the medical device (by measuring relaxation of the protons in the envelope polymer) and the other image the body tissue (by measuring relaxation of the protons in water and lipds contained in the body tissue or blood). Both images can be superimposed so that the physician obtains combined information in one image. Due to the detection of protons in the soft polymer and not in water molecules surrounding the medical device a more confined and significantly sharper artifact can be achieved which is almost limited to the actual diameter of the medical device.

This envelope polymer preferably has a T1 relaxation time of 1 to 100 ms, more preferably 1 to 500 ms, and most preferably 1 to 1000 ms, and a T2 relaxation time preferably of 0.1 to 1 ms, more preferably 0.1 to 5 ms and most preferably 0.1 to 10 ms.

In a further embodiment of the present invention the medical device has a stably attached coating on its outer surface. This coating preferably is lubricious. The stably attached coating material is obtained by compounding the envelope polymer with one or more chemical compounds having functional groups, preferably carboxy groups or amino groups. Embedding the rods in this modified envelope polymer preferably is achieved by an extrusion process. Subsequently the surface functional groups, preferably the carboxy groups/amino groups, are reacted with other functional groups, preferably with amino groups/carboxy groups, respectively, to obtain a covalent bond, preferably an amide bond. The residual functional groups (e.g. the remaining carboxy/amine groups) are then chemically crosslinked by a crosslinker.

The above described different aspects of the invention can be combined with each other.

Figure 1B:
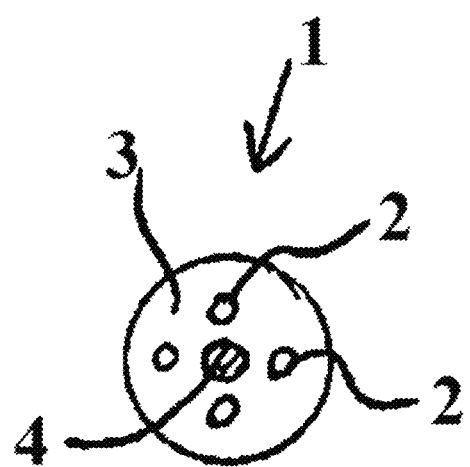
Figure 2A:
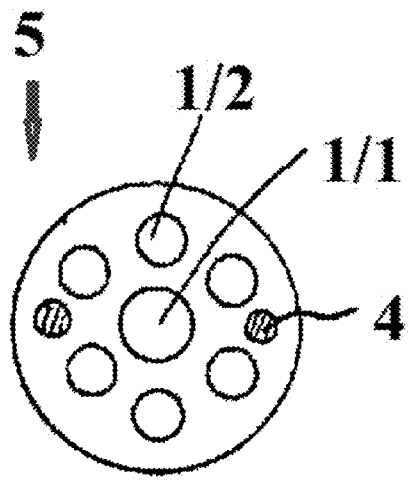
Figure 2B:
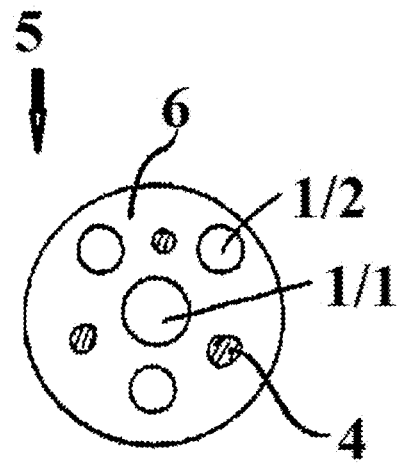
Figure 3A:
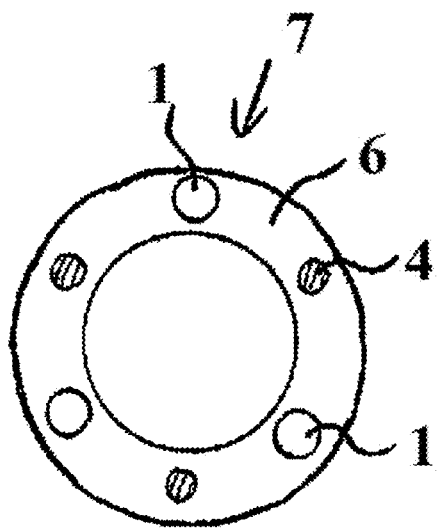
Figure 3B:
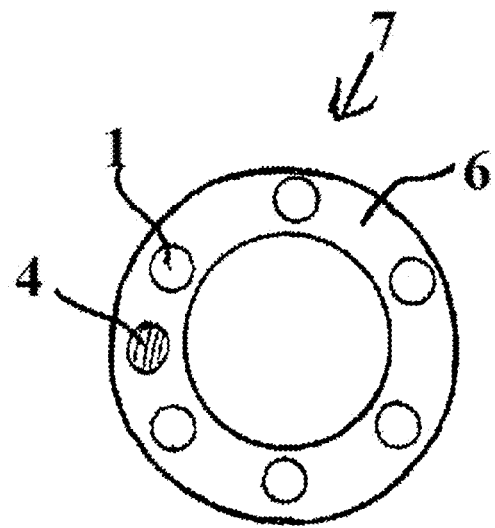

The invention will now be exemplified in more detail on the basis of the embodiments illustrated in the drawings in which:

FIG. 1A shows a rod shaped body according to the invention in a perspective view, FIG. 1B shows the rod shaped body according to FIG. 1A in a cross-sectional view, FIGS. 2A, 2B show guidewires according to the present invention in cross-sectional views, FIGS. 3A, 3B show catheters according to the present invention in cross-sectional views, FIGS. 4A to 4H show images which have been created by the test equipment by means of MR or X-ray imaging, FIGS. 5A-5C provide a list of medical devices, FIGS. 6 and 7 show images which have been created using the test samples or combinations of the test samples by means of MR imaging.

Some of the present prototypes are realized with aramide fibers. In the following detailed description of the present invention the terms "aramide fiber" and "aramide filaments" are used as synonym to ht-fibers. Aramide fibers were chosen due to its tensile strength. Thus it is clear for someone skilled in the art that the aramide fibers can be replaced by other non-electrically conductive fibers having the same or even better tensile strength.

The first aspect of the present invention relates to a rod shaped body 1 (in the following: rod) which forms an intermediate product for producing medical devices. The rod shaped body according to the present invention is a further development of the rod shaped bodies as described in WO 2007/000148 A2 and WO 2009/141165 A2. Therefore, full reference is made to the disclosure of these documents and those documents are incorporated here by reference.

The rod 1 comprises one or more non-metallic filaments 2 and a non-ferromagnetic matrix material 3 (in the following: matrix). The non-metallic filaments 2 are electrically nonconductive filaments. Electrically conductive filaments would lead to electric current in and heating of the guidewire induced by the magnetic and RF fields during MR imaging. Such rods can comprise metal particles but these particles must be separated from each other so that they do not create electrically conductive sections of more than 10 to 15 cm, preferably not more than 5 to 10 cm. The matrix material encloses and/or agglutinates the filaments. The rods 1 are usually doped with marker particles for generating a signal in an X-ray or MR imaging process. These particles are embedded in the matrix 3. However, it can also be desirable to have an undoped rod 1 without any marker particles.

A basic characteristic and advantage of the rods 1 is that different rods 1 can be doped with different marker particles, whereas in a medical device differently doped and/or undoped rods 1 can be incorporated. This will be explained in more detail below in the description of the different versions of medical devices according to the present invention. Simply by use of differently doped rods various medical devices having different characteristics in X-ray or MR imaging processes can be easily and cost-efficiently manufactured in the same process by replacing one rod by another one.

FIG. 1A schematically displays a rod 1 in a perspective view. The filaments 2 of the rod 1 are long filaments 2 which are directed in the longitudinal direction of the rod 1. These filaments 2 extend along the major part of the rod 1. This means that the length of the filaments 2 is at least half of the length of the rod 1. Preferably, the length of the filaments 2 extends along the total length of the rods 1 or at least 80% of the total length of the rods 1.

Such long filaments 2 provide a high strength to the rods 1 in longitudinal direction. Medical devices comprising these rods frequently are designed for being introduced into a blood vessel, an organ (e.g. heart, liver, kidney or lung) or the brain. Therefore, a strong force can be applied to these medical devices in longitudinal direction during introduction of these devices into the body cavity or when pulling them out thereof. This force is taken up by the rods 1.

On the other hand the medical devices have to provide a certain flexibility to advance them along curves of the body cavity. By arranging the filaments 2 in longitudinal direction of the rods 1, rods are obtained having both a high stability/strength in longitudinal direction and an appropriate flexibility in lateral direction.

The filaments 2 are usually made of glass fibers. It is also possible that the reinforcing fibers are ceramic fibers, polyamide or aramid, e.g. Kevlar® fibers, as long as the fibers provide the necessary strength in longitudinal and lateral direction. It is possible to also use other kinds of fibers as long as the fibers do not provide electric conductivity. Long fibers of electrically conductive material cannot be incorporated into medical devices being used in an MRI process.

Glass fibers are available in different qualities. These different qualities are called E-glass (E=electric), S-glass (S=strength), R-glass (R=resistance), M-glass (M=modulus), D-glass (D=dielectric), C-glass (C=corrosion), ECR-glass (E-glass corrosion resistant). The tensile strength, the tensile modulus and the elongation to failure of E-glass, D-glass and R- or S-glass is shown in the following table:

|  | Tensile strength (MPa) | Tensile modulus (GPa) | Elongation to failure (%) |
| --- | --- | --- | --- |
| E-glass | 3400 | 73 | 7.7 |
| D-glass | 2500 | 55 | 4.5 |
| R- or S-glass | 4400 | 86 | 5.1 |

Saint-Gobain offers under the trade name Quartzel® a glass fiber with even a higher strength, namely a tensile strength of 6000 MPa, a tensile modulus of 78 GPa and an elongation to failure of 7.7%.

A group of several filaments 2 being arranged in parallel to each other is called a roving. The rod 1 is produced by means of the micro-pultrusion process. Thereby such a roving is pultruded together with the matrix material in which the marker particles can be contained. The amount of filaments has a strong influence on the mechanical properties of the rods.

Yarns can be used instead of rovings for the production of the rods 1. In such yarns the filaments 2 are drilled or braided. However, rovings are preferred as the drilled or braided structure of the yarns may cause a corresponding structure at the surface of the rods. Rods having a smooth surface instead of such a structured surface are preferred because it is easier to use them in a subsequent extrusion process to obtain a smooth surface of the respective medical device.

Glass fibers usually are quantified and characterized in "Tex" which means g/m. Filaments 2 used in the rods 1 usually are in the range of 10 to 100 Tex, more preferred 30 to 70 Tex. The diameter of the rods usually is in the range of 0.10 mm to 0.30 mm.

The amount of the matrix material, which preferably is epoxy resin, defines the capacity for incorporated marker particles. Therefore, it is preferred to have several filaments uniformly distributed or preferably located at the circumferential section of the rod to provide the rod with a high mechanical strength without occupying a to large part of the cross section area of the rod. The lower the number of filaments the weaker is the mechanical strength of the rod. This even applies if the lower number of filaments is compensated by a higher diameter of the filaments. Therefore, it is preferred that the number of filaments is at least four, or more, e.g. at least six or at least ten.

According to a further aspect of the present invention the rod 1 comprises in addition to the filaments 2 a cord 4. The cord 4 is embedded in the matrix material 3. The cord 4 consists of a material with a higher flexibility than the filaments 2 such as polyamide filaments, aramide filaments, polyethylene terephthalate (PET) filaments, rayon filaments (e.g. HL fiber), cotton filaments, or hemp filaments. The cord 4 extends along the total rod and is directed in the longitudinal direction of the rod. Such a cord does not break if it is bent. On the other hand the longitudinal strength of such a cord 4 having the same cross sectional area as a filament 2 usually is weaker than the longitudinal strength of the filaments 2.

If the rod 1 or a medical device incorporating such a rod 1 breaks, the broken parts are still connected by means of the cord 4. Thereby, it is ensured that even if such a breakage occurs in the human or animal body during the medical intervention the broken parts can be safely pulled out. The cord 4 is advantageously arranged in the center of the rod 1.

Aramide filaments provide the functions of both the cord as well as the non-metallic filaments. Thus, a medical device comprising one rod having an aramide filament which is arranged in parallel, twisted, braided, woven or in another type of assembly, is preferred. Twisted, braided, woven filaments form a spatial structure which is preferred in combination with a flexible filament such as aramide filaments.

Aramide filaments are flexible and have a high tensile strength. As in such a spatial structure the filaments are running in different directions in the body of the medical device the high tensional rigidity of the filaments causes also a high stiffness of the composite material consisting of the fibers or filaments, respectively, and the matrix material.

In the following the mechanical structure of medical devices comprising several of the rods 1 is explained:

FIG. 2A and FIG. 2B each show a guidewire 5 in a cross-sectional view. Such a guidewire 5 is a medical device which frequently is inserted into a blood vessel whereby preferably a flexible tip at the distal end of the guidewire supports easy access to a certain place in a human or animal body. If the position of the guidewire is correct then other medical devices can be advanced along the guidewire.

The medical device, particularly the guidewire, according to the present invention comprises several rods 1 and an envelope polymer 6. The envelope polymer 6 preferably is a biocompatible material. Such biocompatible materials are available on the market e.g. under the trade names Mediprene® or Tecoflex™. Tecoflex™ is an elastic polymer material which is based on polyurethane (PU). Mediprene® is a thermoplastic elastomer made from SEBS (styrene-ethylene-butylene-styrene-elastomer) which is primarily used for medical purposes. Mediprene is offered by Elasto AB, Sweden. Other appropriate polymers are e.g. polyethylene, polypropylene, EVA, PVP and silicone. The envelope polymer can also be made from other biocompatible materials, such as a soft biocompatible polymer material or rubber material or soft PVC.

The flexible and elastic envelope polymer 6 provides a certain shape to the medical device and encloses the rods. Hence, the medical devices consist of a multi-composite material comprising the rods 1 as a kind of reinforcing material and the envelope polymer 6 as embedding and agglutinating material. The mechanical properties of a medical device are mainly defined by the mechanical properties, the number, the dimensions, and the arrangement of the rods 1.

In a preferred embodiment the envelope polymer is modified by compounding, i.e. mechanically mixing, it with chemical compounds having one or more functional groups, preferably amino and/or carboxy groups. These chemical compounds are preferably polycarboxylic acids (e.g. polyacrylic acids), polyvinylamine, polyethyleneimine, acroleinacrylic acid copolymer or polyallylamine Particularly preferred is a compound of Mediprene® and polycarboxylic acid. Most preferably a sodium salt solution of polycarboxylic acid (e.g. POC AS 5060, Evonik Industries, Essen, Germany) is blended with Mediprene® polymer to obtain an amount of 5, 10, 20, 30 or 40 or more than 40% (w/w) POC in Mediprene®. All amounts therebetween are also suitable and may be used. This modified envelope polymer is then used in an extrusion process to embed and agglutinate the rods. After the extrusion the free carboxy groups at the surface are reacted preferably with polyvinylamine or other polyamino polymers to result in an amide linkage. Remaining free amino groups are then crosslinked preferably with a short-chain (e.g., $C_1$-$C_6$) hydrophilic alpha-omega homobifunctional crosslinker to provide the stably attached, preferably lubricious, coating at the surface of the medical device. These modified surfaces are suitable to incorporate passive-positive markers as defined and described below (e.g. gadolinium (Gd) ions or complexes, or cerium (Ce), praseodymium (Pr), neodymium (Nd), promethium (Pm), samarium (Sm), europium (Eu), terbium (Tb), dysprosium (Dy), holmium (Ho), erbium (Ed, thulium (Tm), ytterbium (Yb) and lutetium (Lu) ions or complexes).

According to the embodiment shown in FIG. 2A there are a central rod 1/1 and peripheral rods 1/2. The central rod is positioned in the center of the guidewire 5. The peripheral rods 1/2 are positioned circumferentially to the central rod 1/1 and the lateral surface of the guidewire 5. The embodiment comprises six peripheral rods 1/2 which are equally spaced apart from each other. The filament content of the central rod 1/1 is 66 Tex. The diameter of the central rod is about 0.20 mm to 0.30 mm. The filament content of the peripheral rods 1/2 is 33 Tex and the diameter is about 0.17 to 0.20 mm. The diameter of the guidewire 5 is about 0.81 mm (0.032 inch). In a stiffer version of this guidewire the diameter of the guidewire is increased to about 0.88 mm (0.035 inch). The filament content can be increased up to at least 100 Tex for the central rod 1/1 and up to at least 45 Tex for the peripheral rods 1/2.

The embodiment shown in FIG. 2A comprises furthermore two cords 4 which are embedded in the envelope polymer 6. These cords 4 have the same purpose and function as the cords 4 which are embedded in the rods 1 as described above. Having the cords 4 embedded in the envelope polymer 6, it is not necessary to use rods 1 having such a cord 4.

Providing the cords 4 in the envelope polymer 6 allows to use cords 4 having a larger diameter as cords which are included in the rods 1. However, it is more difficult to produce the medical devices having cords in addition to the rods. Such medical devices are produced by co-extrusion, wherein the envelope polymer 6 is extruded together with the rods 1 and the cords 4.

FIG. 2B shows another embodiment of a guidewire 5 comprising one central rod 1/1 and three peripheral rods 1/2. In this guidewire 5 three cords 4 are embedded in the envelope polymer 6.

The central rod 1/1 has a filament content of 33 Tex and has a diameter of about 0.20 mm. The peripheral rods 1/2 also have a filament content of 33 Tex but have a smaller diameter of about 0.17 mm. The total diameter of the guidewire 5 is 0.81 mm. The guidewire 5 according to the embodiment of FIG. 2B has a lower stiffness in comparison to the guidewire of FIG. 2A. The filament content can be decreased down to at least 12 Tex or lower for the central rod 1/1 and the peripheral rods 1/2.

The embodiments shown in FIG. 2A and FIG. 2B are mere examples. An advantage of the present invention is that due to the composite structure of the medical devices the mechanical properties, e.g. guidewires, can be individually adapted to the required interventional application by variation of the geometries (i.e. number, dimensioning and positioning of the rods 1/1 and 1/2). Furthermore, guidewires may not contain a central rod 1/1 but only peripheral rods 1/2. Minimally, a guidewire contains only one rod.

Actually there are the following classes of guidewires which are classified only according to their mechanical properties:

1) Stiff or Super-Stiff Guidewires

A stiff or super-stiff guidewire has a diameter of 0.88 to 0.97 mm (0.035-0.038 inch). The central rod 1/1 has a fiber content of 66 Tex or higher, wherein up to about 100 Tex can be appropriate. At least five, preferably at least 6 or more peripheral rods 1/2 are provided. The fiber content of the rods is in the range of 20 to 40 Tex. The envelope polymer 6 is preferably made of a polymer with a shore hardness of at least 40 D, preferably 60 D and more preferably 72 D.

2) Standard Guidewire

The standard guidewire typically has a diameter in the range of 0.81 to 0.88 mm (0.032-0.035 inch). The central rod preferably has a fiber content of 20 to 40 Tex. The standard guidewire preferably comprises 2 to 4 peripheral rods 1/2. The peripheral rods preferably have a fiber content of 20 to 40 Tex. The envelope polymer may be made of a soft, medium or hard polymer material. The softer the envelope polymer is, the stiffer the rods 1/1, 1/2 have to be designed. Due to the peripheral position of the peripheral rods 1/2 a small increase of the stiffness of the peripheral rods significantly increases the total stiffness of the guidewire. Therefore, the total stiffness of the guidewire can easily be adapted in a wide range by selecting different peripheral rods.

3) Standard Micro Guidewire

A standard micro guidewire has a diameter of about 0.36 to 0.41 mm (0.014-0.016 inch). The central rod has a fiber content of preferably 15 to 33 Tex, more preferably 20 to 25 Tex. The micro guidewire preferably comprises 1 to 3 peripheral rods. The fiber content of the peripheral rods preferably is about 10-20 Tex. The envelope polymer is preferably made of a polymer material having a shore hardness below 72 D, more preferably below 60 D and even more preferably below 40 D. According to another embodiment the standard micro guidewire comprises only one rod having a fiber content of preferably 50 to 100 Tex, more preferably 55 to 80 Tex. This rod comprises a passive-positive MRI marker such as iron (Fe) particles. The concentration of the passive-positive MRI marker in the matrix is in the range of 1:10 to 1:100 and preferably in the range of 1:40 to 1:60. The particle size of the passive-positive MRI marker particle preferably is about 40 µm to about 65 µm.

4) Super Flexible Micro Guidewire

The super flexible micro guidewire has a diameter of about 0.25 to 0.36 mm (0.010-0.014 inch) and preferably 0.28 to 0.33 mm (0.011-0.013 inch). It does not have a central rod. It comprises 2 or 3 peripheral rods. The peripheral rods have a glass fiber content of preferably 10-20 Tex. The envelope polymer is preferably made of a polymer having a shore hardness below 60 D and more preferably below 40 D.

5) Stiff Micro Guidewire

A stiff micro guidewire has a diameter of about 0.25 to 0.46 mm (0.010-0.018 inch). It consists of one rod 1 without any envelope polymer. The fiber content of the rod preferably is about 30 to 120 Tex, and in particular 60 to 100 Tex. To avoid disruption of a broken guidewire it is preferred that it comprises at least one aramide filament. The stiff micro guidewire comprises preferably at least one aramide filament and at least one glass fiber and in particular, several aramide filaments and several glass fibers. Such a combination of different filaments in one rod ensures that the rod does not disrupt after breakage and has a sufficiently high stiffness resulting from the glass fibers.

These classes of guidewires are typical examples. As mentioned above reinforcing fibers for the rods, particularly glass fibers, are available in different qualities. If glass fibers with a higher stiffness or strength, respectively, are used then the stiffness can be accordingly adapted by the mechanical properties resulting from the other materials of the guidewire, or from the number of the rods, or from the arrangement of the rods, or from the embodiment of the rods (particularly with respect to the fiber content and the diameter of the rods). The above examples demonstrate that due to the multi-composite structure the medical devices can be designed with a wide range of mechanical properties. These are independent of the visibility in an X-ray and/or MR imaging process as described further below.

If a guidewire having a central rod and peripheral rods is bent then the peripheral rods are more elongated and compressed than the central rod. To improve the flexibility of the guidewire it is appropriate to have more extensible glass fibers in the peripheral rods than in the central rod, i.e. the glass fibers of the peripheral rods have a lower tensile modulus than the glass fibers of the central rod. This means that the central rod provides a high stiffness and the peripheral rods provide a high elasticity so that the guidewire has the necessary flexibility and stiffness.

A medical device, particularly a guidewire, according to the present invention may comprise a flexible tip. Such a flexible tip can be produced separately and be attached to the medical device by polymer welding. The separately produced flexible tip is made of an elastic and weldable polymer e.g. polyurethane. The elastic tip is connected to the rod by chemical welding or thermo welding. The stiffness of the flexible tip can increase from the end which is connected to the medical device, e.g. the guidewire, to the other (distal) end of the flexible tip. Preferably, the stiffness at the connected end is similar to the stiffness of the medical device, e.g. the guidewire. This can be achieved e.g. by reducing the diameter of the flexible tip in the direction from the connected to the distal end.

In another embodiment the flexible tip of a medical device, esp. a guidewire, preferably is made by the following steps:

Grinding of a circumferential layer of the guidewire at one end so that at least an outer part of the envelope polymer is removed in this grinded section of the guidewire. Peripheral rods or a part of a central rod can also be removed by grinding. If the guidewire does not have an envelope polymer at least a part of the rod is removed by grinding.

The grinded part of the guidewire is coated with a flexible polymer material to form the flexible tip. The flexible polymer material may distally extend beyond the grinded section so that the flexible tip comprises a very soft end and an intermediate section which is reinforced by rod material. The flexible polymer can be any kind of flexible polymer, e.g. PEBAX 3533 SA01 med.

The length of the distal flexible tip preferably is 5 to 30 cm, more preferably 8 to 20 cm and particularly preferably 10 to 15 cm.

Independent of whether the flexible tip is produced separately and attached to the rod, or whether it is produced by coating a core part of the rod, it is preferable that the flexible tip has the shape of a cone with a decreasing diameter from the connected to the distal end. The flexible tip can be provided with an X-ray and/or MR marker. The marker can be one of the passive markers described below which is either blended to the material of the tip or which is coated to the tip.

The concentration of the MRI markers can be designed in such a way that the flexible tip causes MRI artifacts with a higher, the same or a lower intensity than the residual part of the medical device.

Generally in the medical devices according to the present invention no electrically conducting parts are used because they cause large artifacts during MRI and lead to heating of the medical device. However, it can be appropriate to provide metallic particles or a metallic core in the flexible tip because then due to the artifacts the tip is clearly distinguishable from the residual part of the medical device. Of course it has to be accepted that the artifacts of the tip disturb the image in the vicinity of the tip. Therefore, it can also be appropriate to have in the flexible tip a combination of the markers according to the below described embodiments. The tip can also be reinforced by means of short glass fibers.

The gradient and the stiffness of the flexible tip can also be realized by reducing the diameter of a central core of the flexible tip wherein the core is made of a material which is harder than the main material of the flexible tip.

FIG. 3A and FIG. 3B each show a cross-sectional view of a catheter 7. Such a catheter 7 has the form of a tube wherein the catheter wall is made of the composite material comprising the rods 1 and the envelope polymer 6. As the rods 1 are placed further apart from the center of the catheter when compared to the arrangement in the guidewire 5 a smaller number of rods 1 or less stiff rods 1 are sufficient to obtain the same strength in lateral direction as in a corresponding guidewire 5.

The embodiment according to FIG. 3A comprises three rods 1 each having a filament content of 33 Tex and a diameter of about 0.17 mm to 0.20 mm. The embodiment of FIG. 3B comprises six rods 1. In both embodiments at least one cord 4 is embedded in the envelope polymer 6.

The design of the catheters according to the present invention can be classified into the following two groups:
1) Standard Catheters (5 F to 6 F)

The diameter of catheters usually is defined by the unit "French" wherein 3 French correspond to 1 mm. A catheter having a diameter of 5 F to 6 F (1.66 to 2.00 mm) according to the present invention is embodied with a wall thickness in the range of 0.20 to 0.30 mm. It comprises rods with a fiber content of about 20 to 40 Tex and preferably 25 to 35 Tex. The number of rods is in the range of 3 to 8 and preferably 3, 5 or 6.

2) Micro Catheters (2 F to 4 F)

A micro catheter has a diameter of 2 F to 4 F (0.66 to 1.33 mm) and the wall thickness is in the range of 0.10 to 0.25 mm. The rods have a fiber content of about 10 to 20 Tex.

In a catheter the rods are spaced wider apart from each other than in a guidewire. Therefore, bending a catheter causes the rods to be bent stronger than in a guidewire. The rods of a catheter therefore should have good elastic properties. The fibers for the rods of a catheter are preferably made of a material, particularly a glass fiber, having a high tensile modulus (E-modulus) of at least 65 GPa and preferably of at least 70 GPa.

An alternative embodiment of the catheter contains the rods braided into the envelope polymer.

Another alternative embodiment of a tube or catheter comprises at least two concentric layers wherein the different layers may have the same or different thickness and at least two layers consist of different polymers or polymer grades. These polymers may be chosen from any polymer materials, e.g. Mediprene®, polyurethane (e.g. Tecoflex™), polyethylene, polypropylene, EVA, PVP, silicone, PEBAX, or PEEK. Such tube or catheter comprises at least one MRI marker. One of the layers can be provided with a passive-negative MRI marker. Preferably, only the most inner layer comprises a passive-negative MRI marker. Alternatively, the inner and/or the outer layer may be coated with a passive-positive MRI marker.

This embodiment can be provided optionally with non-metallic filaments. The filaments can be twisted, braided, woven to a spatial structure, particularly to a tube like structure which is embedded in the polymer material. With such a spatial structure it is preferred that the filaments comprise ht-fibers. A combination of ht-fibers and glass fibers allows to adjust the rigidity of the catheter or tube in a wide range.

FIGS. 5A-5C show a table in which several medical devices are listed. This table contains four columns. In the first column the type of medical device is defined. In the second column the design of the device is described. The design of the device is defined by the number and the characteristics of the rods and by description of the envelope polymer. In the third column the filament content of the rods and the corresponding diameters are specified. The fourth column provides examples for appropriate interventional applications for the corresponding medical device.

The medical devices listed in the table of FIGS. 5A-5C provide certain mechanical properties defined by the design of the device and the design of the rods as given in this table. The visibility of the medical devices can be adjusted individually and independent of the mechanical properties by doping the rods and/or the envelope polymer with suitable marker particles as disclosed below.

This table discloses besides guidewires and catheters also puncture needles which are thin, short hollow needles. The puncture needle (B) does not necessarily comprise a rod but can be embodied as a thin hollow tube made of epoxy resin and reinforced with glass fibers. Such a puncture needle can be regarded as a hollow rod wherein this puncture needle can be doped in the same way as the above described rods. The rovings comprising a plurality of long glass fibers arranged in parallel can be flattened before they are embedded in the epoxy resin for forming a puncture needle. Thereby a very small wall thickness can be achieved.

The puncture needles can also be produced by embedding thin rods into a hard matrix. Such a matrix can be e.g. epoxy resin. The thin rods and the epoxy resin are co-micropultruded for production of the puncture needles.

Independent of whether the puncture needle is embodied as a thin hollow tube made of epoxy resin and reinforced with glass fibers or whether it is produced by co-micropultrusion of flattened glass fibers in epoxy resin, the wall at the distal end of the puncture needle preferably is endowed with a thin, sharp edge. This edge can be provided by a hard layer of polymer, e.g. a distinctly hard epoxy resin, covering the end of the puncture needle. Under this layer the glass fibers of the puncture needle are securely covered and protected.

The rods, the matrix material and/or the glass fiber reinforced epoxy resin can be doped by any marker described in the examples of the rods and medical devices as disclosed below. Also any combination of markers is possible. Likewise the puncture needles can be provided with the above described coating containing gadolinium ions on their outer surface. Such a coating can also be provided on the inner surface of the hollow puncture needle.

The envelope polymer of the above described medical devices is made from a biocompatible material such as an elastic polymer material which is based on polyurethane (PU) or a thermoplastic elastomer made from SEBS (styrene-ethylene-butylene-styrene-elastomer). Other appropriate polymers are e.g. polyethylene, polypropylene, EVA, PVP and silicone. As described further below softer polymer materials can be advantageous in combination with MRI markers. If a softer polymer material is used as envelope polymer then the rods have to be designed stiffer to compensate the softer envelope polymer.

In the following the X-ray markers which were tested in prototypes are explained:
Type 1: Doping of one rod 1/1 of the guidewire 5 or of one rod of catheter 7 or another device with tungsten nanoparticles.
Type 2: Doping of envelope polymer with 5 to 80% barium sulphate, preferably 20% to 40% barium sulphate, most preferably 40% barium sulphate.
Type 3: combination of types 1 and 2

The weight ratio of the doping particles and the matrix material 3, preferably epoxy resin, in case of tungsten nanoparticles preferably is 1:1 to 2:1, and in case of iron microparticles preferably is 1:5 to 1:100, more preferably 1:10 to 1:70, most preferably 1:30 to 1:60, if not specified differently, and in case of tungsten microparticles preferably is 1:1 to 4:1, more preferably 2:1 to 3:1. In the following the weight ratio of the matrix material 3 and the doping particles is called "concentration".

Tungsten microparticles can also be provided in the envelope polymer. With tungsten microparticles as an X-ray marker an envelope polymer better maintains its elasticity and becomes less brittle than being doped with barium sulphate. Therefore, tungsten microparticles are very advantageous if they are used to dope an envelope polymer, e.g. a polyurethane, with an X-ray marker.

Figure 4A:
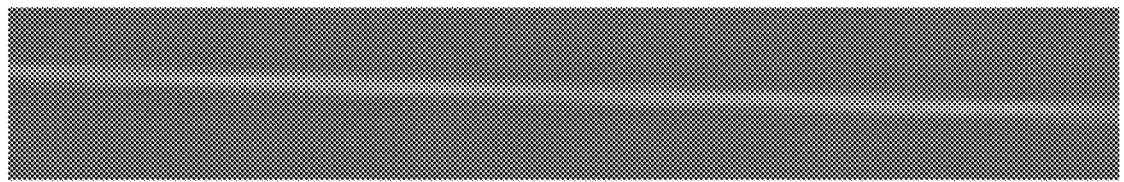

X-ray markers can be included in all of the above listed medical devices to obtain visibility in X-ray angiography and similar X-ray imaging procedures comparable to current medical devices on the market which contain e.g. metal cores or metal braids. The concentration of the X-ray markers is dependent on the design of the device, especially the volume of the epoxy resin for Type 1 and of the envelope polymer 6 for Type 2, or the combination of these respectively. For visualization in computer tomography (CT) a lower amount of marker particles and/or less strong radiopaque marker particles are recommended. E.g., one rod doped with a 2:1 concentration of tungsten nanoparticles alone has proven to be sufficient for CT in guidewire prototypes. An image of a single rod doped with tungsten nanoparticles with a 2:1 concentration and having a diameter of 0.20 mm placed in a water phantom is shown in FIG. 4A. This image shows a clear and sharp image of the rod.

Examples of X-ray angiography markers, e.g. for guidewires and catheters:
1) tungsten nanoparticles with a concentration of 2:1 to 1:1 in one or more rods and 40% barium sulfate in envelope polymer;
2) tungsten nanoparticles with a concentration of 2:1 to 1:1 in one or more rods and 20% barium sulfate in envelope polymer.

Other suitable X-ray markers are Barium (Ba), tantalum (Ta), osmium (Os), praseodymium (Pr), platinum (Pt), gold (Au), and lead (Pb).

Figure 4B:
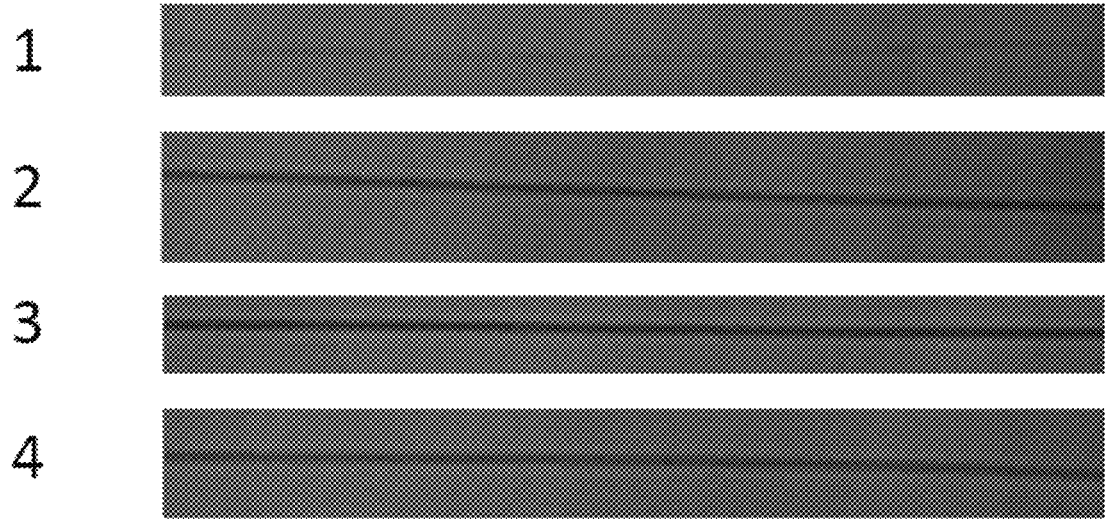

FIG. 4B shows images which were taken by X-ray angiography using a water phantom. The images are assigned with the numbers 1-4 wherein the images show the following samples or devices:
Image 1: a single rod doped with tungsten nanoparticles with a 2:1 concentration and a diameter of 0.20 mm.
Image 2: a guidewire with 40% barium sulphate in the envelope polymer and a central rod (33 Tex) doped with tungsten nanoparticles 2:1 with a diameter of 0.20 mm and three peripheral rods (33 Tex) doped with iron microparticles (<150 μm) with a 1:10 concentration and a diameter of 0.17 mm; the diameter of the guidewire is 0.81 mm (0.032 inch).
Image 3: a Terumo reference guidewire with a nitinol core and a polymer envelope (specification: REF-GA32263M); the diameter is 0.81 mm (0.032 inch).
Image 4: a guidewire with 40% barium sulphate in the envelope polymer, an undoped central rod having a diameter of 0.20 mm and three peripheral rods (33 Tex) being doped with iron microparticles (<150 μm) in a concentration of 1:10. The peripheral rods have a diameter of 0.17 mm and the guidewire has a diameter of 0.81 mm (0.032 inch).

The images 2 to 4 show the respective guidewire clearly and precisely. The image of the rod is rather vague. This shows that tungsten nanoparticles are not sufficient for a one time X-ray exposure as it is performed in X-ray angiography. Nevertheless, the contribution of the tungsten doped rod to signal intensity in X-ray angiography is significant and useful.

In the following the MRI markers which were tested in prototypes are explained:
The MRI markers used for doping of the rods and/or the envelope polymer are ferromagnetic, paramagnetic and diamagnetic particles. Ferromagnetic and paramagnetic particles have positive magnetic susceptibility characteristics. Such particles in the following are called passive-positive markers. Diamagnetic particles have negative magnetic susceptibility characteristics and are therefore called passive-negative markers. Passive-negative markers are for example barium sulphate and lead. Passive-positive markers are iron (Fe), iron oxide (FeO, $Fe_2O_3$, $Fe_3O_4$), cobalt (Co), nickel (Ni), molybdenum (Mo), zirconium (Zr), titanium (Ti), manganese (Mn), rubidium (Rb), aluminum (Al), palladium (Pd), platinum (Pt), chromium (Cr) or chromium dioxide ($CrO_2$). These markers due to their susceptibility characteristics have an influence on the magnetic field in the direct vicinity of the rods or the medical devices. This local magnetic field influences the relaxation time of protons contained in adjacent water molecules. In the literature there are also other classifications of MRI markers. E.g. it is referred to Kanischka Ratnayaka et al., review "Interventional cardiovascular magnetic resonance: still tantalizing"; Journal of Cardiovascular Magnetic Resonance, Dec. 29, 2008, in which the MRI markers are defined by their effects on the image whether they cause negative contrast through local distortions of the magnetic field (black spots) or positive contrast through enhanced local signal (bright spots). However, for describing the present invention it is preferred to define the MRI markers according to the physical characteristics, namely susceptibility characteristics.

Also iron-platinium alloy nanoparticles (FePt NPs) can be used as passive-negative MRI markers. In Shu Chen et al.; "Engineered Biocompatible Nanoparticles for in Vivo Imaging Applications" the use of FePt NPs as contrast agent for MRI is described.

Passive MRI markers cause either negative contrast through local distortions of the magnetic field (black spots) or positive contrast through enhanced local signal (bright spots). Ferromagnetic and paramagnetic particles, e.g. iron, iron oxide, nickel, aluminum and others, are called passive negative markers which generate signal voids from intentional magnetic susceptibility artifacts. Gadolinium, dysprosium and similar metals are passive positive markers as they reduce the proton spin relaxation time of associated water molecules. Due to their specific characteristics and influences on the magnetic properties (especially the relaxation time) of the protons in the water molecules located directly adjacent to the rods or medical devices these MRI markers can be detected by common water-proton adjusted MRI sequences.

Prototypes of the rods and medical devices were tested in MRI systems. In these tests the rods and medical devices were placed in a water bath (water phantom) so that they were completely surrounded and covered by water. This water phantom was placed into the magnetic field of an MR scanner. There are standard measuring conditions ("MR sequences") in MRI systems for detection of the position and properties of the water-protons in the local magnetic field. With these standard sequences the rods and medical devices containing different MRI markers were tested. Standard MRI sequences employed on a Siemens Magnetom Symphony 1.5 Tesla MR scanner essentially were:

1) T1 Weighted Sequence

SE 2D, TR/TE=420/14 ms, slice thickness: 2.0 mm, FOV=400×400 mm, matrix: 512×256, phase FOV: 100%, percent sampling: 50%, bandwidth: 90 Hz/px, flip angle: 90°, TA=111 s, total number of slices: 15, spacing between slices: 2.2 mm (10%), phase encoding steps: 256

2) T2 Weighted Sequence

TSE (SE) 2D, TR/TE=3690/104 ms, slice thickness: 1.9 mm, FOV=400×400 mm, matrix: 512×307, phase FOV: 100%, percent sampling: 60%, bandwidth: 130 Hz/px, flip angle: 180°, TA=90 s, total number of slices: 15, spacing between slices: 2.09 mm (10%), phase encoding steps: 345 (307), echo train length (turbo factor): 15

3) VIBE Sequence

GRE/FLASH 3D, TR/TE=4.3/2.05 ms, slice thickness: 1.0 mm, FOV=400×300 mm, matrix: 256×134, averages: 2, phase FOV: 75%, percent sampling: 69.79%, bandwidth: 490 Hz/px, flip angle: 12°, TA=14 s, total number of slices: 16, phase encoding steps: 134, slab thickness: 16

4) Gradient Echo Sequence (GRE)

GRE/FLASH 2D, TR/TE=700/12 ms, slice thickness: 2.5 mm, FOV=400×400 mm, matrix: 512×256, phase FOV: 100%, percent sampling: 50%, bandwidth: 65 Hz/px, flip angle: 30°, TA=179 s, total number of slices: 15, spacing between slices: 2.75 mm (10%), phase encoding steps: 256

5) Real-Time Sequence

2D SSFP, >1 frame/s, TR/TE=2.2/4.7 ms, slice thickness: 5 mm, FOV=224×224 mm, matrix: 224×224, flip angle: 60°, voxel size 1×1 mm FIG. 4C shows four images A1, A2, B1 and B2 which were taken with a T2 weighted sequence using a water phantom. The images A1 and A2 show a single rod doped with iron oxide nanoparticles at a concentration of 1:20 and the images B1 and B2 show a guidewire with a central rod (33 Tex) doped with tungsten nanoparticles at a concentration of 2:1 and having a diameter of 0.20 mm and three peripheral rods (33 Tex) doped with iron oxide nanoparticles (<50 nm) at a concentration of 1:20 having a diameter of 0.17 mm. The diameter of the guidewire is 0.81 mm (0.032 inch). In the images A1 and B1 the rod or guidewire, respectively, is arranged orthogonally to the magnetic field $B_0$. The images A2 and B2 were taken with the rod or guidewire, respectively, arranged in parallel to the magnetic field $B_o$. The artifact of the rod and guidewire in the images A2 and B2 is very weak contrary to the images A1 and B1. Hence, when arranged orthogonally to the magnetic field $B_0$ of the MR scanner they provided good results. However, if the nanoparticle containing rods or guidewires are arranged in parallel to the magnetic field $B_o$ of the MR scanner they do not provide any reasonable signal except of a displacement artifact. The nanoparticles are homogeneously distributed in the matrix material of the rods. Due to the high number of the small nanoparticles the distance between neighbouring nanoparticles is very small. It is assumed that due to this small distance the magnetic moments are coupled to each other so that all the nanoparticles act as one bar magnet which extends in the longitudinal direction of the rods or medical devices. If this is the case then the magnetic field in the direct vicinity of the rods or the medical device containing the rods is only very weakly influenced by the magnetism of the nanoparticles because the magnetic field is concentrated inside the rods or medical device. However, if the medical device is arranged orthogonally to the magnetic field $B_o$ of the MR scanner then the magnetic nanoparticles are also coupled with each other and can be regarded as virtual bar magnets. However, then the bar magnets are arranged laterally to the longitudinal direction of the rods. At the end of each virtual rod magnet the magnetic field is concentrated so that in the direct vicinity of the rods or medical device the magnetic field is strongly influenced by the magnetism of the nanoparticles. Therefore, a rod doped with nanoparticles, particularly iron oxide nanoparticles, is only visible if arranged orthogonally to the magnetic field $B_o$ of the MR scanner. Medical devices containing such rods can be used in open magnet MR scanners because in these the medical devices are used mainly in a direction orthogonal to the magnetic field $B_o$. Such rods or such a medical device produces a very sharp and precise image with nearly no artifacts in an open magnet MR scanner.

However, today most of the installed MR scanners are based on ring magnets in which the medical devices should also be detectable if they are arranged in parallel to the magnetic field $B_0$. Therefore, the distance between the individual marker particles should be high enough to avoid such a coupling and to also generate good signals in parallel direction to the magnetic field $B_0$. To achieve such distances and to have a sufficiently high doping effect the size of the marker particles should be larger.

Rods doped with iron particles with a diameter of 4-6 μm and with iron particles sieved with a mesh of 150 μm, respectively, and guidewire test samples containing such rods were tested. These guidewire test samples consisted of a polymer tube in which the rods are placed for simulating a guidewire in an imaging process. The guidewire test samples additionally comprised one rod doped with tungsten nanoparticles (concentration 2:1, diameter 0.20 mm).

The images resulting from these tests are shown in FIG. 4D and FIG. 4E. The images of FIG. 4D show a rod doped with iron particles with a diameter of 4-6 μm (image A1, A2) and the rod doped with iron particles sieved with a mesh of 150 μm (image B1, B2). In the images A1 and B1 the test samples were arranged orthogonally to the magnetic field $B_0$. In the images A2 and B2 the test samples were arranged in parallel to the magnetic field $B_0$. The tests were carried out with a T2 weighted sequence in a water phantom. FIG. 4E shows corresponding images of a guidewire test sample having one rod doped with iron microparticles (4-6 µm, concentration 1:10 diameter 0.17 mm) in the images A1 and A2 and a guidewire test sample having a rod doped with iron microparticles sieved with a mesh of 150 µm (concentration 1:10, diameter 0.17 mm) in the images B1 and B2. These images were made applying a real-time sequence and using an aortic phantom. In the images A1 and B1 the guidewire test samples were arranged orthogonally to the magnetic field $B_0$ and in the images A2 and B2 in parallel to the magnetic field $B_0$. As it can be seen in the images the test samples were visible independent of whether they were arranged orthogonally or in parallel to the magnetic field $B_o$. Iron is a strong ferromagnet. Therefore, it makes the protons in water molecules in the vicinity of the medical device visible in a water-proton adjusted MR sequence. Iron creates strong artifacts and thereby causes device images which are much broader than the device itself. This is the case particularly if the medical device or the rods, respectively, are arranged orthogonally to the magnetic field $B_o$ of the MRI imaging system.

With respect to the doping with passive MRI markers the goal is to have a) a strong signal and b) a confined and sharp signal. However, the stronger the signal is, the bigger are the artifacts which reduce the sharpness of the image. Preferably, the signal in parallel (strong enough) and orthogonal direction (not to broad) should be reasonably balanced.

The following effects were found which influence the intensity and the sharpness of the signal:

The higher the concentration of the markers is, the stronger is the signal.

The larger the particles are, the better is the balance between imaging in parallel and orthogonal direction. However, the size of the particles is limited by the production process of the rods and/or the medical device. Particle sizes in the range of 1 µm to 150 µm are most appropriate. Preferably, the particles have a size of at least 1 µm, 2 µm, 5 µm, 10 µm or 50 µm. Good results are also achieved with particles which are sieved with a mesh of 150 µm. Furthermore a mesh of about 80-130 µm is also suitable.

Figure 4G:
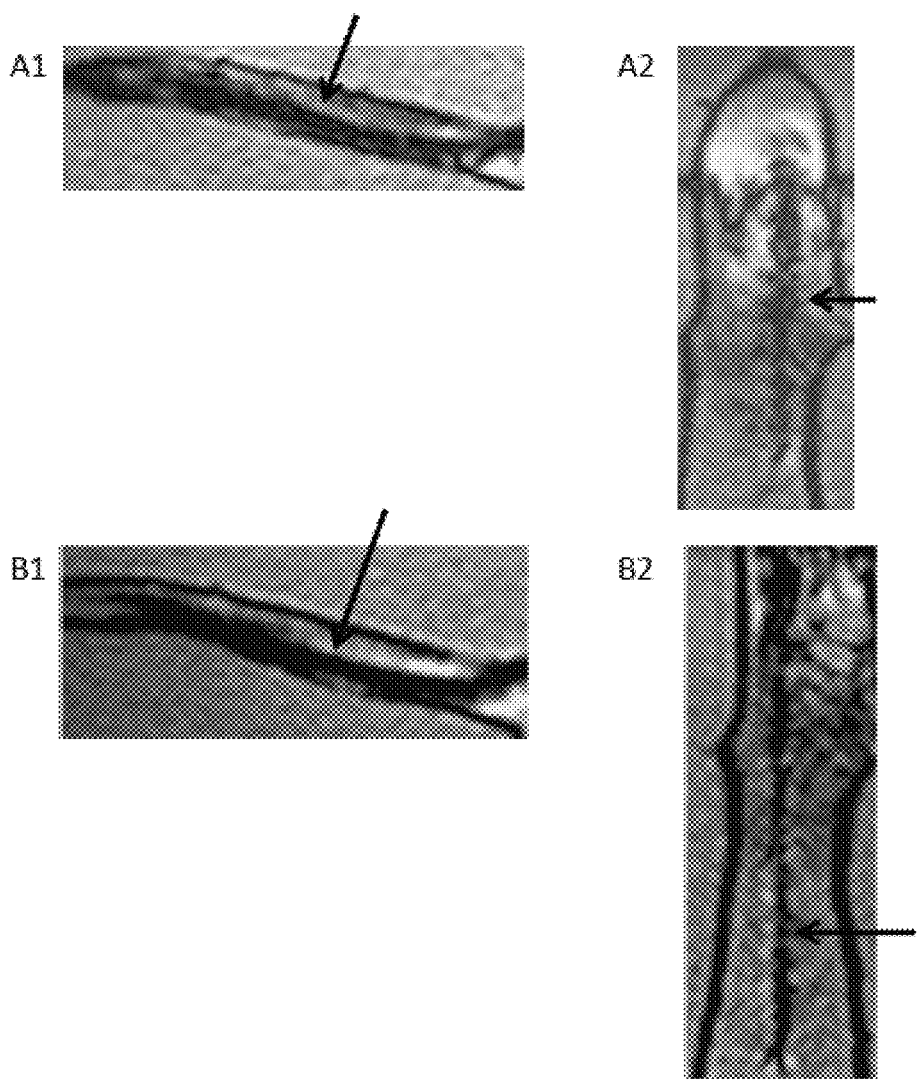

A plurality of doped rods provides a stronger signal than only a single rod comprising the same or even a higher amount of marker particles. FIG. 4F shows a guidewire test sample comprising one rod doped with tungsten nanoparticles in a concentration of 2:1 and a diameter of 0.20 mm and three rods (image B1, B2) doped with iron particles sieved with a mesh of 150 µm in a concentration of 1:10 and a diameter of 0.17 mm and another guidewire test sample comprising the same kind of rods but with only one rod doped with tungsten and one rod doped with iron particles (image A1, A2). FIG. 4G shows images of a guidewire test sample having one rod doped with tungsten nanoparticles (concentration 2:1, diameter 0.20 mm) and one rod doped with iron microparticles sieved with a mesh of 150 µm (concentration 1:10, diameter 0.17 mm) in the images A1 and A2 and a guidewire test sample having one rod doped with tungsten nanoparticles (concentration 2:1, diameter 0.20 mm) and three rods doped with iron microparticles sieved with a mesh of 150 µm (concentration 1:100, diameter 0.17 mm) in the images B1 and B2. These images were made applying a real-time sequence and using an aortic phantom. Although the higher doped rod according to the images A1 and A2 of FIG. 4G contains ten times the amount of marker particles than the lower doped rods according to the images B1 and B2 of FIG. 4G, the three lower doped rods together cause a stronger signal than the one higher doped rod. This can be explained in that the plurality of doped rods is localized further apart in the medical device so that the range of influence onto the magnetic field covers a broader area. Therefore, more voxels (which are detected by the MR scanner) are influenced by the plurality of rods. Concluding, an increased number of voxels is blackened in comparison to a guidewire having only one doped rod. More blackened voxels mean a visually broader and stronger signal.

The distance of the marker particles or rods, respectively, from the surrounding water molecules influences the sharpness and intensity of the signal. The larger the distance between marker particles and neighbouring water molecules is, the weaker is the influence of the magnetic field on these water molecules. In other words, the thicker the layer of an envelope polymer is with which the rods are covered in the medical device, the sharper the signal will be. Thus the position of the rods in the medical device has a strong influence on the sharpness of the signal.

FIG. 6 shows images A and B which were taken with a T2 weighted sequence using a water phantom. FIG. 7 shows similar images A and B which were taken with a Gradient echo sequence (GRE). The images A and B in both figures show the following samples numbered with 1-7:

1. rod shaped body, 33 Tex, OD 0.17 mm (=Outer Diameter) (without envelope polymer);
2. rod shaped body, 66 Tex, OD 0.24 mm (without envelope polymer);
3. stiff guidewire, OD 0.88 mm;
4. standard guidewire, OD 0.81 mm;
5. micro guidewire, OD 0.31 mm;
6. standard guidewire, OD 0.81 mm; inserted into a tube with ID 1.5 mm (=Inner Diameter) and OD 2.3 mm;
7. standard guidewire, OD 0.81 mm; inserted into a tube with ID 0.94 mm and OD 1.45 mm;

All guidewire samples contain rods doped with iron particles 40-63 µm at a concentration of 1:50. The standard guidewire comprises a central rod with 33 Tex glass fiber. The stiff guidewire comprises a central rod with 66 Tex glass fiber. The micro guidewire comprises a rod with 66 Tex glass fiber covered by a thin envelope polymer (PU). It must be noted that the amount of the matrix material is approximately proportional to the amount of glass fibers. Therefore, rods having 66 Tex glass fiber comprise more matrix material than rods having 33 Tex glass fiber. As the concentration of the marker in the matrix material is always the same the rods having 66 Tex glass fiber absolutely contain more marker particles than rods having 33 Tex glass fiber.

The samples 6 and 7 comprise a guidewire being inserted into a tube. The tubes are sealed so that no water can penetrate into the air gap between guidewire and tube wall. Sample 6 encloses a relevant air gap. In sample 7 the air gap between the tube and the guidewire is small.

In image A the samples are arranged longitudinally to the magnetic field $B_o$ and in image B orthogonally to the magnetic field $B_o$.

The rods (samples 1 and 2) show a broad artifact. Also the micro guidewire (sample 5) having only a thin envelope polymer shows a broad artifact. The artifacts generated by the standard and stiff guidewires are significantly smaller.

The larger air gap of sample 6 causes a black artifact which adds to the artifact of the MRI marker so that the image of the sample is darker in comparison to the sample 7 with a small airgap.

By comparing the samples 4 and 7 it can be seen that the tube covering the guidewire with only a small air gap reduces the width of the artifact.

These results demonstrate that the envelope polymer of the guidewires (sample 3 and 4) and the tube (sample 7) reduce the width of the artifacts compared to the respective rods. This is caused by the larger distance between the water molecules surrounding the respective sample and the passive-negative MRI marker particles. The larger the distance is the smaller is the artifact.

As the rod shaped bodies in a medical device mostly are arranged in different positions with respect to the center of the medical device it is preferred that the rod shaped bodies positioned more distant to the center of the medical device contain no passive-negative MRI marker. This principle is embodied in a guidewire preferably in such a way that the rod shaped body containing a passive-negative MRI marker is located in the center of the guidewire. If the guidewire comprises several rod shaped bodies then it is useful if the rod shaped bodies being not in the center do not comprise passive-negative MRI markers.

This principle can also be applied to a catheter. If a catheter comprises at least one rod shaped body having a passive-negative MRI marker then this rod shaped body is positioned at the inner section of the catheter. Rod shaped bodies having no passive-negative MRI marker may be positioned closer to the circumferential surface of the catheter. Such a catheter or tube can also be embodied of at least two concentric layers wherein only the most inner layer comprises a passive-negative MRI marker.

The width of the artifact is mainly determined by the distance of the passive-negative MRI marker to the circumferential surface of the medical device as the magnetic influence of the marker on the surrounding water molecules detected in MRI depends on this distance. This is also valid for catheters and tubes as the water molecules surrounding the outer surface of the medical device determine the outer border of the artifacts and not the water molecules in the inner lumen of a catheter or tube. The distance between the section containing a passive-negative MRI marker and the outer circumferential surface of the medical device preferably is at least 0.1 mm, more preferably at least 0.2 mm and most preferably at least 0.3 mm.

These effects can be exploited in different combinations to achieve the above mentioned aim of a strong and sharp signal. Basically, the size of the particles should be sufficiently large to balance the signals detected in longitudinal and orthogonal direction to the magnetic field $B_o$ of the MR scanner.

A strong and comparably confined and sharp signal can be achieved when the absolute amount of marker particles is kept rather low and distributed in several peripheral rods.

Figure 4H:
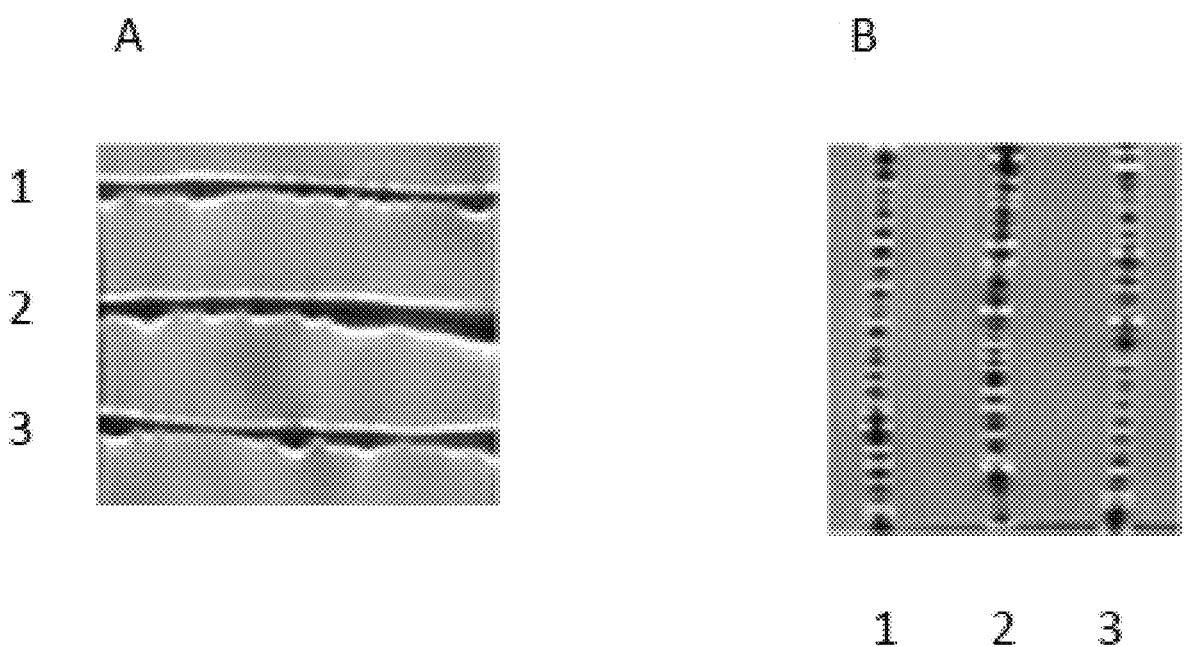

Another possibility is to embody the medical device with a central rod or with the rods positioned closest to the center of the medical device being doped with a passive MRI marker and having peripheral undoped rods (which contain no passive MRI marker) or rods doped with an X-ray marker. FIG. 4H comprises an image A and B, wherein in each image three individual rods 1, 2, 3 are shown, each being doped with iron microparticles (<150 μm, concentration 1:10, diameter 0.17 mm). The rod 2 is uncovered. The rod 1 is covered by a thick layer of epoxy resin, so that the total diameter of this sample is 0.9 mm. The rod 3 is covered by a thick layer of polyurethane polymer. The total diameter of this sample is also about 0.9 mm Image A shows the rods arranged orthogonally to the magnetic field $B_o$ and image B in parallel to the magnetic field $B_o$. In the image A it is clearly visible that the uncovered rod causes a much broader signal than the two other covered rods. As the rods 1 and 3 are covered by an envelope polymer the magnetic field distortion outside of the medical device is attenuated. As a result only a comparably small layer of surrounding water molecules is influenced by the iron particles in the rod, compared to a reasonably thicker layer when the marker particles are located in the peripheral rods close to the outer boundary of the medical device. The thicker the layer of influenced water molecules is, the broader is the resulting signal/artifact. Concluding, the MR image of the medical device has a multiple of its actual diameter. In case of a medical device in which the central rod comprises the MRI marker particles a sufficiently strong and sharp image is obtained, having only a minimally larger diameter than the actual diameter of the device.

These designs of the medical device are based on the influence of the magnetic field caused by the passive-negative marker particles on the protons in the water molecules present in the direct vicinity of the medical device.

Another approach to obtain a strong, confined and sharp signal is adjustment of the MR sequence. If the relaxation echoes of protons in the envelope polymer and not of those in the surrounding water molecules are detected a very sharp image limited almost to the actual diameter of the medical device can be obtained. This is most preferable e.g. for the tips of puncture or biopsy needles where absolutely precise operation of the device to target small e.g. cancer tissue regions is required. Hard polymer materials such as epoxy resins or the above mentioned polyurethane (PU) or thermoplastic elastomer made from SEBS contain a plurality of protons but relaxation times for these protons are much too short in hard polymers due to the stiffness of the materials in order to be detected with currently established MR sequences and scanners. Instead of these relatively hard polymer materials softer polymer materials can be used as envelope polymer for the medical devices according to the invention. In softer polymers the protons are a bit more flexible and have somewhat longer relaxation times. Consequently, they can be detected with current MR scanners and MR sequence software. E.g. PVC or rubber materials are appropriate for that purpose. Rubber materials due to the cross-linked polymer chains provide a sufficiently high stability but the protons of rubber materials still have a sufficiently long relaxation time. The use of such rubber materials in an MR scanner is described in R. Umathum et al., Rubber Materials for Active Device Tracking, Abstract 16$^{th}$ ISMRM Congress 2008 in Toronto (The International Society for Magnetic Resonance in Medicine). Such rubber materials can also be extruded, wherein the vulcanization of the rubber material is carried out after the extrusion.

There are also known rubber-like solid hydrogels, such as PVA-H, which provide a very good visibility. However, the strength of such hydrogels is low. Another design of the guidewire comprises a core of such a rubber-like solid hydrogel which is enclosed by the envelope polymer. In the envelope polymer one or more rods can be integrated. In such a guidewire the mechanical stability is mainly defined by the tube-like envelope polymer. In an MR scanner the core of the guidewire provides a signal. This signal can be influenced by doping the core of the guidewire or by means of doped rods in the envelope polymer.

One advantage of using a soft polymer or a rubber polymer as envelope polymer of a medical device or of using a core made of a soft polymer, rubber or a rubber-like solid hydrogel is that the relaxation time is sufficiently long to be detected in an MR scanner. As the relaxation time differs significantly from the relaxation time of water these materials can be detected by a shorter echo time than that for water resulting in two images which can be overlaid. Thereby, the medical device can be distinctly presented, e.g. in a specifically selected colour, and different from the body tissue and blood which is presented as used to in black, white and shades of grey. Additionally, the user can individually select one of the two images to be separately displayed on the screen. Therefore, it is possible to control the position of the medical device in the body by superimposing both images but it is also possible to have an image of the body tissue alone which is not disturbed by the medical device.

A further advantage for visualization of medical devices in MRI guided interventions can be realized if e.g. a guidewire comprises a softer polymer as described above as the envelope polymer but a correspondingly used catheter comprises a harder polymer as the wall-forming polymer. In that case the guidewire is detected with a short echo time resulting in a sharp signal almost precisely delineating its boundaries. The catheter is detected with a longer echo time detecting the artifact resulting from the surrounding water molecules. The two devices may be presented in different colours which very easily enables distinguishing of the catheter from the guidewire.

The following MRI marker particles were used for doping of the rods and the envelope polymer:
- Tungsten nanoparticles: American Elements; Tungsten Nanopowder, 99%, <100 μm (typically 40-60 nm), spherical; product code: W-M-01-NP
- Tungsten microparticles: Sigma-Aldrich; Tungsten, powder, 99.9%, 12 μm; product code: 267511
- Iron microparticles: Riedel de Haen (Sigma-Aldrich), <150 μm; product code: 12312
- Iron microparticles: Roth, 4-6 μm; product code: 3718.0
- Iron oxide nanoparticles: Sigma-Aldrich, <50 nm; product code: 544884
- Barium Sulphate (e.g. in commercially available "Tecoflex with BaSO4" or "Mediprene with BaSO4")

The following materials were used for production of rods and medical devices:
- High temperature resistant epoxy resin
- Tecoflex™ is an elastic polymer material which is based on polyurethane (PU).
- Mediprene® is a thermoplastic elastomer made from SEBS (styrene-ethylene-butylenestyrene-elastomer) which is primarily used for medical purposes. Mediprene is offered by Elasto AB, Sweden.
- Glass fibers
- Aramide fibers The medical devices were produced by co-extrusion wherein the envelope polymer is extruded together with the rods. As the rods shall not be deformed during the co-extrusion the rods were made from a high temperature resistant material. However, if the envelope polymer is based on a rubber material then the extrusion temperature can be reduced so that the temperature requirements for the matrix material are correspondingly reduced and other resin materials than high temperature resistant epoxy resin are suitable. These other resin materials can be regular epoxy resin, PVC or synthetic rubber.

LIST OF REFERENCE NUMERALS

1 Rod shaped body
1/1 Central rod
1/2 Peripheral rod
2 Filament
3 Matrix polymer
4 Cord
5 Guidewire
6 Envelope polymer
7 Catheter

The invention claimed is:

1. A medical device comprising:
an elongate polymer body;
rod-shaped bodies embedded in the elongate polymer body, wherein at least one of the rod-shaped bodies comprises:
one or more non-metallic filaments; and
a non-ferromagnetic matrix material enclosing and/or agglutinating the one or more filaments,
wherein the rod-shaped bodies are arranged in different positions with respect to the central longitudinal axis of the medical device, wherein rod-shaped bodies positioned near the central axis of the medical device contain marker particles in a matrix material thereof to form a passive- negative magnetic resonance imaging (MRI) marker for generating an artifact in a magnetic resonance imaging process and all rod-shaped bodies positioned more distant to the central longitudinal axis of the medical device contain no marker particles; and
wherein the medical device is a guidewire, mandrel, or stylet, wherein the medical device generates a sufficiently strong and sharp image, by influencing only a comparably small layer of surrounding molecules by the MRI marker particles in magnetic resonance imaging.

2. The medical device according to claim 1, wherein the MRI marker is selected from the group consisting of ferromagnetic particles, paramagnetic particles, and iron microparticles with particle sizes in the range of 1 μm to 150 μm.

3. The medical device according to claim 1, wherein the one or more non-metallic filaments comprise glass fibers.

4. A medical device according to claim 1, wherein the medical device has a maximum outer diameter of 0.97 mm.

5. A medical device according to claim 1, wherein the distance of the passive-negative MRI marker to the outer surface of the medical device is at least 0.1 mm.

6. A medical device according to claim 1, wherein the marker particles are formed of iron, iron oxide, nickel, or aluminum.

7. A medical device comprising:
one or more rod-shaped bodies, wherein at least one of the rod-shaped bodies comprises one or more non-metallic filaments and a non-ferromagnetic matrix material, wherein the matrix material encloses and/or agglutinates the one or more filaments; and
an envelope polymer in which the one or more rod-shaped bodies are embedded, wherein a high tenacity fiber (HT-fiber) is embedded either in the matrix material or in the envelope polymer, wherein the HT-fiber extends along the whole longitudinal direction of the medical device, and
wherein the HT-fiber is more flexible than the one or more non-metallic filaments,
wherein the medical device is a guidewire, catheter, mandrel, stylet, stent, biopsy needle, puncture needle or cannula and contains marker particles only in a central section of the medical device to form a passive-negative magnetic resonance imaging (MRI) marker for generating an artifact in a magnetic resonance imaging process.

8. The medical device according to claim 7, wherein the one or more rod-shaped bodies are arranged in different positions with respect to the center of the medical device and the rod-shaped bodies which are arranged closer to the center of the medical device comprise non-metallic filaments having a higher tensile modulus than the non-metallic filaments of the rod-shaped bodies which are positioned more distant to the center of the medical device.

9. The medical device according to claim 7, wherein the MRI marker is selected from the group consisting of ferromagnetic particles and paramagnetic particles and iron microparticles with particle sizes in the range of 1 µm to 150 µm.

10. The medical device according to claim 7, wherein the one or more non-metallic filaments comprise glass fibers and/or HT-fibers.

11. The medical device according to claim 7, wherein the HT-fiber is embedded in the matrix material.

12. The medical device according to claim 7, having at least one of the following characteristics (i)-(iv):
 (i) the one or more non-metallic filaments extend along the major part of the one or more rod-shaped bodies;
 (ii) the one or more non-metallic filaments consist of multiple non-metallic filaments that are arranged in parallel to each other,
 (iii) the one or more non-metallic filaments extend along the major part of the one or more rod-shaped bodies, and the length of each of the non-metallic filaments is at least half of the length of the one or more rod shaped bodies, and
 (iv) the one or more non-metallic filaments consist of multiple non-metallic filaments that collectively comprise several glass fibers and several HT-fibers.

13. The medical device according to claim 7, comprising more than one rod-shaped body, wherein at least one rod shaped body includes one or more non-metallic filaments comprising glass fibers and another rod-shaped body includes one or more non-metallic filaments comprising HT-fibers.

14. The medical device according to claim 7. wherein the medical device is embodied as said catheter having at least two concentric layers, wherein one of said layers is reinforced by non-metallic filaments being twisted. braided, or woven to a spatial structure.

* * * * *

UNITED STATES PATENT AND TRADEMARK OFFICE
CERTIFICATE OF CORRECTION

| | | |
|---|---|---|
| PATENT NO. | : 11,752,240 B2 | Page 1 of 1 |
| APPLICATION NO. | : 15/586155 | |
| DATED | : September 12, 2023 | |
| INVENTOR(S) | : Klaus Düring et al. | |

It is certified that error appears in the above-identified patent and that said Letters Patent is hereby corrected as shown below:

In the Specification

Column 1, Line 59, "and" should be -- und --.

Column 10, Line 25, "Ed" should be -- Er} --.

Signed and Sealed this
Seventh Day of November, 2023

Katherine Kelly Vidal
*Director of the United States Patent and Trademark Office*